US010585092B2

(12) United States Patent
Lee et al.

(10) Patent No.: US 10,585,092 B2
(45) Date of Patent: Mar. 10, 2020

(54) DEVICES AND METHODS FOR THE RAPID AND ACCURATE DETECTION OF ANALYTES

(71) Applicant: Ohio State Innovation Foundation, Columbus, OH (US)

(72) Inventors: Stephen C. Lee, Dublin, OH (US); Wu Lu, Dublin, OH (US); Leonard J. Brillson, New Albany, OH (US); Gregg A. Hadley, Albany, OH (US); Ronald P. Pelletier, Columbus, OH (US); Paul R. Berger, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 15/407,785

(22) Filed: Jan. 17, 2017

(65) Prior Publication Data

US 2017/0131267 A1    May 11, 2017

Related U.S. Application Data

(63) Continuation of application No. 13/747,921, filed on Jan. 23, 2013, now abandoned.
(Continued)

(51) Int. Cl.
*G01N 27/414* (2006.01)
*G01N 33/543* (2006.01)
(Continued)

(52) U.S. Cl.
CPC ..... *G01N 33/5438* (2013.01); *A61B 5/14735* (2013.01); *A61B 5/14865* (2013.01);
(Continued)

(58) Field of Classification Search
CPC .... G01N 27/3275–3276; G01N 27/414–4148; H01L 29/772–8128
See application file for complete search history.

(56) References Cited

U.S. PATENT DOCUMENTS

| 5,160,597 A | 11/1992 | Colapicchioni et al. |
| 6,203,981 B1 | 3/2001 | Ackley et al. |
(Continued)

FOREIGN PATENT DOCUMENTS

| EP | 0211609 | 2/1987 |
| WO | 2007/109228 | 9/2007 |
| WO | 2010/054159 | 5/2010 |

OTHER PUBLICATIONS

Casal, Patricia, et al. "ImmunoFET feasibility in physiological salt environments," *Philosophical Transactions of The Royal Society*, vol. 370, 2012, pp. 2474-2488.
(Continued)

*Primary Examiner* — J. Christopher Ball
(74) *Attorney, Agent, or Firm* — Meunier Carlin & Curfman LLC

(57) ABSTRACT

Disclosed are field effect transistor-based (FET-based) sensors for the rapid and accurate detection of analytes both in vivo and in vitro. The FET-based sensors can include a substrate, a channel disposed on the substrate, a source electrode and a drain electrode electrically connected to the channel, and a recognition element for an analyte of interest immobilized on the surface of the channel via a linking group. The distance between the recognition element and the channel can be configured such that association of the analyte of interest with the recognition element induces a change in the electrical properties of the channel. In this way, an analyte of interest can be detected by measuring a change in an electrical property of the channel. Also pro-
(Continued)

vided are devices, including probes and multi-well plates, incorporating the FET-based sensors.

20 Claims, 7 Drawing Sheets

Related U.S. Application Data

(60) Provisional application No. 61/589,751, filed on Jan. 23, 2012.

(51) Int. Cl.

| | | |
|---|---|---|
| *A61B 5/1473* | (2006.01) | |
| *A61B 5/1486* | (2006.01) | |
| *A61B 5/00* | (2006.01) | |
| *B01L 3/00* | (2006.01) | |
| *G01N 33/68* | (2006.01) | |
| *H01L 29/20* | (2006.01) | |
| *H01L 29/205* | (2006.01) | |
| *A61B 5/145* | (2006.01) | |

(52) U.S. Cl.
CPC ............ *A61B 5/4851* (2013.01); *B01L 3/502* (2013.01); *B01L 3/5085* (2013.01); *G01N 27/414* (2013.01); *G01N 27/4145* (2013.01); *G01N 33/6863* (2013.01); *H01L 29/2003* (2013.01); *H01L 29/205* (2013.01); *A61B 5/14507* (2013.01); *A61B 5/14546* (2013.01); *A61B 5/413* (2013.01); *A61B 5/6848* (2013.01); *A61B 2562/028* (2013.01); *B01L 2300/0645* (2013.01); *B01L 2300/0829* (2013.01); *B01L 2300/12* (2013.01); *G01N 2333/521* (2013.01); *G01N 2800/245* (2013.01); *Y10T 436/14* (2015.01); *Y10T 436/143333* (2015.01)

(56) References Cited

U.S. PATENT DOCUMENTS

| 7,692,219 | B1 | 4/2010 | Holm-Kennedy |
|---|---|---|---|
| 8,231,268 | B2 | 7/2012 | Krol et al. |
| 2002/0012937 | A1 | 1/2002 | Tender et al. |
| 2005/0110053 | A1 | 5/2005 | Shur et al. |
| 2005/0224346 | A1 | 10/2005 | Holm-Kennedy |
| 2008/0032294 | A1 | 2/2008 | Kawarada |
| 2009/0026082 | A1 | 1/2009 | Rothberg et al. |
| 2009/0152596 | A1 | 6/2009 | Yang et al. |
| 2010/0137143 | A1 | 6/2010 | Rothberg et al. |
| 2010/0188069 | A1 | 7/2010 | Ren et al. |
| 2011/0248698 | A1 | 10/2011 | Kikuchi et al. |
| 2011/0278644 | A1 | 11/2011 | Gao et al. |
| 2012/0267693 | A1 | 10/2012 | Holm-Kennedy |
| 2012/0286763 | A1 | 11/2012 | Matsumoto et al. |
| 2013/0158378 | A1 | 6/2013 | Berger et al. |
| 2013/0288378 | A1 | 10/2013 | Gu et al. |
| 2014/0127675 | A1 | 5/2014 | Ren et al. |

OTHER PUBLICATIONS

Eteshola, Edward, et al., "Engineering functional protein interfaces for immunologically modified field effect transistor (ImmunoFET) by molecular genetic means," *Journal of The Royal Society Interface*, vol. 5, 2008, pp. 123-127.

Bhushan, Bharat, et al., "Nanoscale adhesion, friction and wear studies of biomolecules on silane polymer-coated silica and alumina-based surfaces," *Journal of The Royal Society Interface*, vol. 6, 2009, pp. 719-733.

Gupta, Samit K., "Detection of clinically relevant levels of protein analyte under physiologic buffer using planar field effect transistors," *Biosensors and Bioelectronics*, vol. 24, 2008, pp. 505-511.

Gupta, Samit K., "Development of a planar immunoFET which detects protein analyte in high salt environments," The Ohio State University, 2010, 157 pages.

Gupta, Samit K., et al., "Interfacial design and structure of protein/polymer films on oxidized AlGaN surfaces," *Journal of Physics D: Applied Physics*, vol. 44, No. 3, 2011, 21 pages.

Nicholson, T.R., et al., "Rational enhancement of nanobiotechnological device functions illustrated by partial optimization of a protein-sensing field effect transistor, Proceedings of the Institution of Mechanical Engineers, *Part N: J. Nanoengineering and Nanosystems*," vol. 223, 2009, 14 pages.

Wen, X., Schuette, M. L., Gupta, S., Nicholson III, T. R., Lee, S. C., & Lu, W. (2011). Improved sensitivity of AlGaN/GaN field effect transistor biosensors by optimized surface functionalization. Sensors Journal, IEEE, 11(8), 1726-1735.

International Search Report and Written Opinion, dated Apr. 9, 2013, in connection with corresponding International Application No. PCT/US2013/022687.

R.A. Villamizar, et al. "Fast detection of *Salmonella infantis* with carbon nanotube field effect transistors" Biosensors and Bioelectronics, vol. 24, 2008, p. 279-283.

Bergveld, P. "The Future of Biosensors," Sensors and Actuators A, 1996, 56: 65-73.

Bergveld, P. "A Critical Evaluation of Direct Electrical Protein Detection Methods," Biosensors & Bioelectronics, 1991, 6: 55-72.

Bergveld, P. "Thirty years of ISFETOLOGY: What happened in the 30 years and what may happen in the next 30 years," Sensors and Actuators B, 2003, 88:1-20.

DEVICES AND METHODS FOR THE RAPID AND ACCURATE DETECTION OF ANALYTES

CROSS REFERENCE TO RELATED APPLICATIONS

This application is a continuation application of U.S. application Ser. No. 13/747,921, filed Jan. 23, 2013, which claims the benefit of U.S. Provisional Application No. 61/589,751, filed Jan. 23, 2012, each of which is incorporated herein by reference in its entirety.

STATEMENT REGARDING FEDERALLY SPONSORED RESEARCH OR DEVELOPMENT

This invention was made with Government Support under Agreements CBET 0758579 awarded to Stephen C. Lee and ECCS 0702191 awarded to Wu Lu by the National Science Foundation. The Government has certain rights to the invention.

FIELD

The present disclosure is generally related to devices and methods for the rapid and accurate detection and/or quantification of analytes.

BACKGROUND

Proteins are involved in a variety of physiological and biochemical pathways within organisms. In particular, proteins are potent yet specific transducers in myriad processes which influence aspects of disease formation, defense, and immunity. For example, cytokines, a specific family of proteins, are heavily involved in cellular signaling and trafficking within the immune system. When cytokines (e.g., interleukin 6 (IL-6) or tumor necrosis factor alpha (TNF-α)) are released by cells, they target and bind to specific receptors on cellular membranes. Upon receptor binding, a cascade of intercellular signaling events occurs, ultimately resulting in changes in cellular behavior. In the case of IL-6 and TNF-α, release triggers numerous processes, including inflammatory response.

Due to their specificity and their role in many biochemical pathways, proteins can serve as molecular targets in therapeutic and diagnostic applications (e.g., oncology, transplant rejection, and inflammation). For example, a growing number of proteins have been identified as biomarkers for disease. In some cases, biomarkers manifest themselves early in a disease process, providing an early indicator for a disease state. For example, monokine induced by interferon γ (MIG, CXCL9) has been implicated as a key biomarker which predicts allograft rejection in both murine models and in humans. The detection of such biomarkers offers the potential to improve patient outcomes through earlier and more targeted intervention.

Existing clinical methodologies for identifying and quantifying proteins suffer from significant drawbacks. Enzyme-linked immunosorbent assays (ELISAs) are the most widely used means for protein detection in clinical settings. While ELISAs can effectively detect proteins in vitro, ELISAs are labor intensive, utilize multiple reagents, and require hours to perform. ELISAs are also unable to assay analyte content in vivo or in situ.

Thus, there remains a need for sensitive and efficient means of detecting and/or quantifying analytes which are inexpensive, detect analytes without labels or additional reagents, exhibit exponential responses to surface potential changes mediated by analyte binding, require limited sample preparation, and operate in real-time. In addition, direct assays that can be utilized to detect analytes, including proteins, in vivo or in situ offer the opportunity to address the challenges and costs associated with treating numerous diseases, including transplant rejection, cancer, and inflammation.

SUMMARY

Electrochemical sensors for the detection and quantification of analytes are provided. The sensors can be used to accurately and rapidly detect and quantify analytes of interest in physiological conditions.

The sensors described herein are modified field effect transistors (FETs). FETs comprise a source electrode, a drain electrode, and a semiconductor channel in communication with the source electrode and the drain electrode, such that channel forms a path for current flow between the source electrode and the drain electrode. In FETs, the electrical properties of the channel (e.g., current flow, voltage, impedance, etc.) are sensitive to electric fields in proximity to the channel surface. Therefore, FET architectures can be modified to detect a charged analyte of interest by immobilizing recognition elements for the analyte of interest on the channel surface. The recognition elements are selected such that they bind to the target analyte, and retain the analyte in close proximity to the channel surface. Once bound, the electric field of the analyte modulates the electrical properties of the underlying FET. As a consequence, the analyte of interest can be rapidly detected in real-time (e.g., in less than about five minutes) by measuring a change in an electrical property of the underlying FET.

FET-based sensors have long been considered unable to detect analytes, such as proteins, in physiological conditions (e.g. ≈150 mM $Na^+$) due to ion shielding in physiologic environments. Adherence to this fundamentally flawed classical assessment has precluded the development of immunoFET-based tools for decades. Disclosed herein are FET-based sensors for accurately and reliably sensing analytes, including immunologic analytes, in physiological conditions (e.g., ≈150 mM $Na^+$). The FET-based sensors can be inexpensive, can detect analyte without label, can exhibit exponential responses to surface potential changes mediated by analyte binding, can require limited sample preparation, and can operate in real-time.

The FET-based sensors provided herein can comprise a substrate, a channel disposed on the substrate, a source electrode and a drain electrode electrically connected to the channel, and a recognition element for an analyte of interest immobilized on the surface of the channel. The recognition element can be immobilized on the channel surface via a linking group, or by direct adsorption to the channel surface. The distance between the recognition element and the channel can be configured such that association of the analyte of interest with the recognition element induces a change in the electrical properties of the channel. For example, in some cases, the recognition element is attached to the surface via a linking group which is selected such that the distance between the recognition element and the surface of the channel is less than about 10 nm (e.g., less than about 5 nm). In this way, an analyte of interest can be detected by measuring a change in an electrical property of the channel.

The channel is fabricated from one or more materials that are substantially impermeable to ions under physiological conditions. For example, in some embodiments, the channel comprises a Group III-nitride heterojunction. The Group III-nitride heterojunction can comprise a first Group III-nitride layer and a second Group III-nitride layer, wherein the first Group III-nitride layer and the second Group III-nitride layer have different bandgaps, such that a two-dimensional electron gas is generated inside the Group III-nitride heterojunction. In some embodiments, the first Group III-nitride body is selected from the group consisting of GaN, InN, InGaN, AlGaN, and combinations thereof, and the second Group III-nitride body is selected from the group consisting of AlGaN, GaN, InAlN, AlN, and combinations thereof. In some embodiments, the first Group II-nitride body comprises GaN and the second Group III-nitride body comprises AlGaN.

The recognition group can be selected in view of the analyte of interest, and can be, for example, a molecule that selectively associates with the analyte of interest. For example, the recognition element can be an antibody, antibody fragment, antibody mimetic, peptide, oligonucleotide, DNA, RNA, aptamer, organic molecule, or combination thereof.

The sensors can be used to accurately and rapidly detect and/or quantify an analyte of interest in physiological conditions. Methods for detecting an analyte of interest can comprise contacting the analyte of interest with a sensor, and measuring a change in an electrical property of the channel. Using this method, one can determine the presence of an analyte of interest, determine the concentration of an analyte of interest, or a combination thereof.

The sensors described herein can be integrated into devices to facilitate the detection of analytes both in vivo, ex vivo, and in vitro. For example, the sensors described herein can be integrated into a variety of existing medical devices, research instruments, and vessels (e.g., micro-well plates) to provide a real-time capability for rapidly and accurately assaying the presence of one or more analytes of interest.

For example, probes may be configured with the FET-based sensors. Probes can comprise an elongate member having a proximal end and a distal end, and one or more sensors positioned at the distal end of the elongate member. Probes may further include additional sensors positioned along the length of the elongate member between the proximal end and the distal end. For example, the probe can be configured with sensors appended at known positions on its surfaces, such that upon insertion into tissue or regions surrounding tissue, the sensors will be exposed to analytes present in solid tissue or tissue fluid. If the positions of the sensors are known, concentration of analytes as a function of sensor position in tissue can be determined, and potentially, mapped over time or as a function of position in tissue. Such probes can be used, for example, to monitor a graft recipient for a rejection response.

Also provided are multi-well plates which include sensors deployed in one or more of the microwells of the multi-well plate. Multi-well plates can include a base comprising a first material having a substantially co-planar top and bottom surface, a plurality of microwells disposed in the base, wherein each microwell comprises a solid bottom proximal to the bottom surface of the base, one or more solid side walls, and an opening located on the top surface of the base, and a sensor positioned within one or more of the plurality of microwells. The one or more sensors are configured such that the recognition element of the sensor is in contact with the contents of the microwell in which it is positioned. Such plates can be used, for example, to conduct rapid immunoassays in clinical and research settings.

BRIEF DESCRIPTION OF THE FIGURES

In FIG. 6A, primary analyte receptor (anti-huMIG or SA, respectively) was deployed on ELISA plates, followed by the secondary affinity element (biotinylated anti-huMIG or SA-HRP, respectively). Hatched bars indicate biotinylated huMIG content of samples; black bars represent total huMIG content of samples. FIG. 6B is a plot of the percent change in current as a function of bMIG concentration in solution (squares with continuous line, bMIG; diamonds with dashed line. MIG). Percent change in current was determined from baseline to the exposed analyte source/drain characteristic. Note that FIG. 6A compares the absolute magnitude of absorbance, while FIG. 6B compares the trend of device signal.

FIG. 7A plots the film thickness (in nm) of trivalent (APTES) and monovalent (APDMES) silane polymer films deposited on a SiO$_2$ substrate. FIG. 7B plots the surface roughness (in nm), estimated using RMS (root mean square) and P-V (peak to valley) values, after silane deposition on SiO$_2$ wafers (Error bars represent ±1 s.d.; open bar, SiO$_2$ (reference); bars with horizontal lines, APTES; checked bars, APDMES).

DETAILED DESCRIPTION

Electrochemical FET-based sensors for the detection and quantification of analytes are provided. The sensors can be used to accurately and rapidly detect and quantify analytes of interest in physiological conditions.

Figure 1:
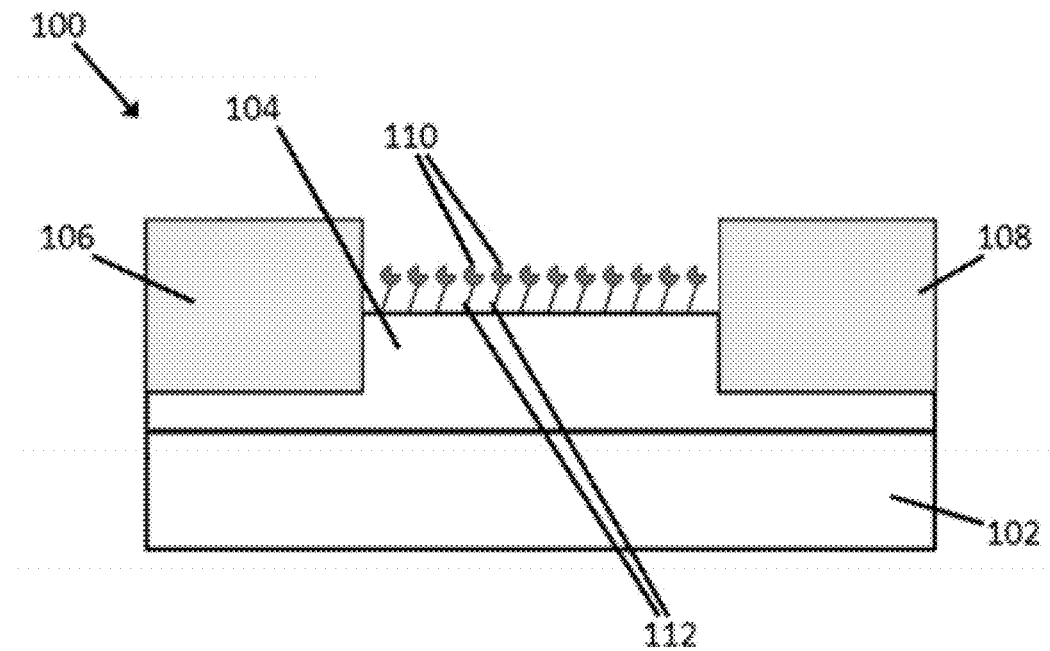
FIG. 1 is a cross-sectional side view of a sensor.

With reference to FIG. 1, the sensor (100) can comprise a substrate (102) and a channel (104) that is disposed on the substrate. The sensor can further include a source electrode (106) and a drain electrode (108) electrically connected to the channel (104). The source electrode (106) and the drain electrode (108) are formed to be separate such that the channel (104) forms a path for current flow between the source electrode and the drain electrode. The sensor also comprises a recognition element (110) for an analyte of interest immobilized on the surface of the channel (104) via a linking group (112).

The substrate can be composed of a variety of materials which are compatible with the overall operation of the FET-based sensor. For example, the substrate may be an electric insulator (i.e., an insulating substrate) or a semiconductor coated with an insulator (i.e., an insulated semiconductor substrate) upon which one or more components of the sensor can be disposed.

Examples of suitable insulating substrates include, but are not limited to, aluminum oxide ($Al_2O_3$), silicon oxide, diamond, silicon nitride, calcium fluoride, glass, and combinations thereof. Examples of suitable insulated semiconductor substrates include semiconductors such as silicon carbide, silicon, aluminum nitride, gallium nitride, zinc oxide, diamond, gallium arsenide, MgZnO, titanium oxide, indium phosphide, and combinations thereof containing an insulating coating. The insulating coating can be formed from any suitable insulator, such as one or more of the insulating substrates described above. In certain embodiments, the substrate comprises Si, SiC, $Al_2O_3$, Group III-nitrides such as AlN or GaN, glass, diamond, or combinations thereof.

The dimensions of the substrate (e.g., length, width, and thickness) are not particularly limited, and can be selected in view of a number of criteria, including the intended application for the sensor and the size of the other sensor components (e.g., the size of the source electrode and/or drain electrode, the size of the channel, and the orientation and/or relative position of the source electrode and drain electrode).

In some embodiments, the substrate is in the form of a plate or chip. In other embodiments, the substrate may be a surface of an article, such as a medical device, probe, research instrument, vial, or microwell plate. In certain embodiments, the substrate has a thickness of at least about 10 microns (e.g., at least about 50 microns, at least about 100 microns, at least about 250 microns, or at least about 500 microns) so as to provide a sensor with sufficient mechanical strength for deployment.

Sensors further comprise a channel disposed on the substrate which forms a current path between the source electrode and the drain electrode. The channel is fabricated from one or more materials so as to be substantially impermeable to ions under physiological conditions. In some embodiments, the sensor comprises a channel fabricated from a material that is substantially impermeable to ions, such that the sensor does not exhibit significant drift in current flow over time when immersed in a physiological buffer solution (e.g., PBS buffer, pH=7.4, 150 mM $Na^+$). In some embodiments, the sensor comprises a channel fabricated from a material that is substantially impermeable to ions, such that the sensor exhibits a drift in current flow of less than about 20% over a period of 10 hours when immersed in a physiological buffer solution (e.g., a drift in current flow of less than about 15% over a period of 10 hours, a drift in current flow of less than about 10% over a period of 10 hours, or a drift in current flow of less than about 5% over a period of 10 hours)

In some embodiments, the channel of the sensor comprises a Group III-nitride heterojunction. The Group III-nitride heterojunction can be formed from a first Group III-nitride layer and a second Group III-nitride layer deposited on the first Group III-nitride layer, wherein the first Group III-nitride layer and the second Group 111-nitride layer have different bandgaps, such that a two-dimensional electron gas (2DEG) is generated inside the Group III-nitride heterojunction. The 2DEG can contain a very high sheet electron concentration in excess of, for example, $10^{13}$ carriers/$cm^2$. Group III-nitride heterojunction of this type are known in the art, and are commercially available, for example, from Cree, Inc. (Raleigh, N.C.). See also, for example, U.S. Pat. No. 5,192,987 to Khan, et al.

As used herein, the term "Group III-nitride" refers to semiconductor compounds formed from nitrogen and the elements of Group III of the Periodic Table, usually aluminum (Al), gallium (Ga) and/or indium (In). The term also refers to ternary and quaternary compounds such as AlGaN and AlInGaN. As is well understood in the art, the Group III elements can combine with nitrogen to form binary (e.g. GaN), ternary (e.g., AlGaN, AlInN) and quaternary (e.g., AlInGaN) compounds. These compounds have empirical formulas in which one mole of nitrogen is combined with a total of one mole of the Group III elements. In some embodiments, the Group III-nitride can be defined by the formula $Al_xGa_{1-x}N$, where x ranges from 0 to 1.

The first Group III-nitride body can comprise, for example, a material selected from the group consisting of GaN. InN. InGaN. AlGaN, and combinations thereof. The second Group III-nitride body can comprise, for example, a material selected from the group consisting of AlGaN, AlN, InAlN, GaN, and combinations thereof. In certain embodiments, the Group III-nitride heterojunction is formed from a first Group III-nitride body that comprises GaN, and a second Group III-nitride body that comprises AlGaN.

The channel can also be formed from a semiconducting layer coated with a passivating layer that renders the channel substantially impermeable to ions under physiological conditions. For example, the channel can be formed from any of the semiconductor materials described above, such as silicon, coated with an $Al_2O_3$ passivating layer.

In these embodiments, the passivating layer can be a thin film of $Al_2O_3$ deposited on the surface of the semiconducting layer. The passivating layer can have a thickness of about 150 nm or less (e.g., about 140 nm or less, about 130 nm or less, about 120 nm or less, about 110 nm or less, about 100 nm or less, about 90 nm or less, about 80 nm or less, about 70 nm or less, about 60 nm or less, about 50 nm or less, about 40 nm or less, about 30 nm or less, or about 20 nm or less). For example, the passivating layer can have a thickness ranging from about 5 nm to about 150 nm (e.g., from about 10 nm to about 100 nm).

The source electrode and drain electrode can be fabricated from any suitable electrical conductors. Examples of suitable electrical conductors include, but are not limited to, gold, platinum, titanium, titanium carbide, tungsten, aluminum, molybdenum, chromium, tungsten silicide, tungsten nitride, and alloys and combinations thereof.

The source electrode and drain electrode, alone and in combination, can be fabricated in any suitable orientation and geometry so as to facilitate sensor operation. At least a portion of the source electrode and drain electrode are positioned in intimate contact with the channel, such that the source electrode and drain electrode are electrically connected. The source electrode and the drain electrode are formed to be separate, such that the channel (to which both the source electrode and the drain electrode are electrically connected) forms a path for current flow between the source electrode and the drain electrode.

The distance between the source electrode and the drain electrode (i.e., the length of the channel) can be selected in view of a number of factors, including the nature of the analyte being measured, the characteristics of the solution in which the analyte is being measured, and overall considerations regarding sensor design and use. In some embodiments, the distance between the source electrode and the drain electrode at their nearest point is less than 5 microns (e.g., less than 1 micron, less than 750 nm, or less than 500 nm). In other embodiments, the distance between the source electrode and the drain electrode at their nearest point is greater than 5 microns. For example, the distance between the source electrode and the drain electrode at their nearest point can range from about 0.5 microns to about 5 mm (e.g., from about 1 micron to about 1 mm; from about 5 microns to about 750 microns, from about 10 microns to about 500 microns, from about 25 microns to about 350 microns, or from about 50 microns to about 200 microns).

Recognition elements can be immobilized on the channel surface via a linking group, or by direct adsorption to the channel surface. In some embodiments, the recognition elements can are immobilized on the surface of the channel via a linking group. The linking group can be selected such that the distance between the recognition element and the channel such that association of the analyte of interest with the recognition element induces a change in the electronic properties of the channel. In some cases, the linking group is selected such that the distance between the recognition element and the surface of the channel is less than about 10 nm (e.g., less than about 9 nm, less than about 8 nm, less than about 7 nm, less than about 6 nm, less than about 5 nm, less than about 4 nm, less than about 3 nm, less than about 2 nm, or less than about 1 nm).

In some embodiments, the linking group comprises a polyvalent linking group. Polyvalent linking groups are derived from polyvalent linkers (i.e., linkers which associate with the channel surface via two or more chemical moieties and have the capacity to be covalently or non-covalently linked to a recognition element). For example, the polyvalent linking group can be derived from a small molecule linker that forms two or more covalent bonds with the channel surface and a covalent bond with the recognition element.

In some embodiments where the linking group comprises a polyvalent linking group, the recognition element is bound to an interfacial polymeric film, such as a silane polymer film derived from trialkoxysilane monomers. In principle, any polymer producing an interfacial film of suitable thickness (e.g., less than 10 nm, less than about 9 nm, less than about 8 nm, less than about 7 nm, less than about 6 nm, less than about 5 nm, less than about 4 nm, less than about 3 nm, less than about 2 nm, or less than about 1 nm) and with capacity to be linked to recognition elements (covalently or non-covalently) can serve as a polyvalent linking group. Examples of suitable polyvalent linking groups include thin films derived from polyvalent linkers including 3-aminopropyl)triethoxysilane (APTES), (3-glycidvloxypropyl) trimethoxysilane, (3-mercaptopropyl) trimethoxysilane, vinyltrimethoxysilane, allyltrimethoxysilane, (3-bromopropyl) trimethoxysilane, triethoxyvinylsilane, triethoxysilane aldehyde (TEA), and combinations thereof.

In certain embodiments, the linking group comprises a monovalent linking group. Monovalent linking groups are derived from monovalent linkers (i.e., linkers which associate with the channel surface via a single chemical moiety and have the capacity to be covalently or non-covalently linked to a recognition element). For example, monovalent linking groups can possess a first moiety which is associated with or bound to the channel surface, and a second moiety which is associated with or bound to the recognition element. In this way, the monovalent linker forms a molecular monolayer which tethers the recognition element to the channel surface.

The monvalent linking group can be derived from a heterobifunctional small molecule which contains a first reactive moiety and a second reactive moiety. The first reactive moiety can be reactive with the channel surface (e.g., with the Group III-nitride heterojunction) and the second reactive moiety can be reactive with one or more moieties present in the recognition element. In some embodiments, the monvalent linking group comprises an alkyl group having from 1 to 6 carbon atoms in its backbone.

In some embodiments, the monovalent linking group is derived from a linker which comprises a monoalkoxysilane moiety. In some embodiments, the monovalent linking group is derived from a linker which comprises a monohalosilane moiety. Examples of suitable monovalent linkers include (3-aminopropyl) dimethylethoxysilane (APDMES), (3-glycidoxypropyl) dimethylethoxysilane, (4-chlorobutyl) dimethylchlorosilane, and combinations thereof.

Sensors further include a recognition element for an analyte of interest immobilized in proximity to the channel surface, such that association of the analyte of interest with the recognition element induces a change in the electrical properties of the channel.

Recognition elements for particular analytes of interest are known in the art, and can be selected in view of a number of considerations including analyte identity, analyte concentration, and the nature of the sample in which the analyte is to be detected. Suitable recognition element include antibodies, antibody fragments, antibody mimetics (e.g., engineered affinity ligands such as AFFIBODY® affinity ligands), peptides (natural or modified peptides), proteins (e.g., recombinant proteins, host proteins), oligonucleotides, DNA, RNA (e.g., microRNAs), aptamers (nucleic acid or peptide), and organic small molecules (e.g., haptens or enzymatic co-factors).

In some embodiments, the recognition element selectively associates with the analyte of interest. The term "selectively associates", as used herein when referring to a recognition element, refers to a binding reaction which is determinative for the analyte of interest in a heterogeneous population of other similar compounds. Generally, the interaction is dependent upon the presence of a particular structure (e.g., an antigenic determinant or epitope) on the binding partner. By way of example, an antibody or antibody fragment selectively associates to its particular target (e.g., an antibody specifically binds to an antigen) but it does not bind in a significant amount to other proteins present in the sample or to other proteins to which the antibody may come in contact in an organism.

In some embodiments, a recognition element that "specifically binds" an analyte of interest has an affinity constant ($K_a$) greater than about $10^5$ $M^{-1}$ (e.g., greater than about $10^6$ $M^{-1}$, greater than about $10^7$ $M^{-1}$, greater than about $10^8$ $M^{-1}$, greater than about $10^9$ $M^{-1}$, greater than about $10^{10}$ $M^{-1}$, greater than about $10^{11}$ $M^{-1}$, greater than about $10^{12}$ $M^{-1}$, or more) with that analyte of interest.

In certain embodiments, the recognition element comprises an antibody. The term "antibody" refers to natural or synthetic antibodies that selectively bind a target antigen. The term includes polyclonal and monoclonal antibodies. In addition to intact immunoglobulin molecules, also included in the term "antibodies" are fragments or polymers of those immunoglobulin molecules, and human or humanized versions of immunoglobulin molecules that selectively bind the target antigen. The term encompasses intact and/or full length immunoglobulins of types IgA, IgG (e.g., IgG1, IgG2, IgG3, IgG4), IgE, IgD, IgM, IgY, antigen-binding fragments and/or single chains of complete immunoglobulins (e.g., single chain antibodies, Fab fragments, F(ab')2 fragments, Fd fragments, scFv (single-chain variable), and single-domain antibody (sdAb) fragments), and other proteins that include at least one antigen-binding immunoglobulin variable region, e.g., a protein that comprises an immunoglobulin variable region, e.g., a heavy (H) chain variable region (VH) and optionally a light (L) chain variable region (VL). The light chains of an antibody may be of type kappa or lambda.

An antibody may be polyclonal or monoclonal. A polyclonal antibody contains immunoglobulin molecules that differ in sequence of their complementarity determining regions (CDRs) and, therefore, typically recognize different epitopes of an antigen. Often a polyclonal antibody is derived from multiple different B cell lines each producing an antibody with a different specificity. A polyclonal antibody may be composed largely of several subpopulations of antibodies, each of which is derived from an individual B cell line. A monoclonal antibody is composed of individual immunoglobulin molecules that comprise CDRs with the same sequence, and, therefore, recognize the same epitope (i.e., the antibody is monospecific). Often a monoclonal antibody is derived from a single B cell line or hybridoma. An antibody may be a "humanized" antibody in which for example, a variable domain of rodent origin is fused to a constant domain of human origin or in which some or all of the complementarity-determining region amino acids often along with one or more framework amino acids are "grafted" from a rodent, e.g., murine, antibody to a human antibody, thus retaining the specificity of the rodent antibody.

In certain embodiments, the recognition element comprises an immunoglobulin G (IgG) antibody, a single-chain variable fragment (scFv), or a single-domain antibody (sdAb).

In certain embodiments, the recognition element comprises a receptor, such as a soluble receptor, for use in detecting ligands of the receptor as the analyte of interest.

In some embodiments, the recognition element comprises an antigen or antigenic hapten. In certain embodiments, the antigenic hapten is not biotin or a derivative thereof. Any suitable antigen can be used. For example, the antigen can be viral antigens, bacterial antigens, tumor antigens, tissue specific antigens, fungal antigens, parasitic antigens, human antigens, botantical antigens, non-human animal antigens, allergens, synthetic antigens, or combination thereof.

In certain embodiments, the recognition element is a recognition element for monokine induced by interferon γ (MIG), a recognition element for interferon gamma-induced protein 10 (IP-10), a recognition element for chemokine (C-C motif) ligand 5 (CCL5), or combinations thereof.

The sensors described herein can further contain one or more additional components. For example, sensors can further comprise an insulator disposed on the source electrode, the drain electrode, or combinations thereof. The insulator can be configured to permit a conductive fluid to be applied to the surface of the channel without the conductive fluid completing a short circuit between the source electrode and the drain electrode. Insulators can also be disposed on a portion of the channel surface, for example, to create a well into which fluid samples can be applied.

Sensors can further include a gate electrode configured to apply a gate bias to the channel. A gate bias can be applied to the channel to allow the sensor to operate in the sub-threshold regime. This can allow the sensor to be more sensitive to interaction of the recognition element with the analyte of interest. In some embodiments, the sensor is back-gated (i.e., it includes a gate electrode beneath the channel, such as within the substrate, which is configured to apply a gate bias to the channel). The sensor can include a side gate positioned adjacent to the channel, and configured to apply a gate bias to the channel. In some embodiments, a floating electrode in contact with the fluid in which the sensor is immersed is used to apply the gate bias.

The sensor can further include electronic circuitry configured to detect a change in an electrical property of the channel. For example, the sensor can include electronic circuitry configured to measure a change in current flow, a change in voltage, a change in impedance, or combinations thereof.

Figure 2:
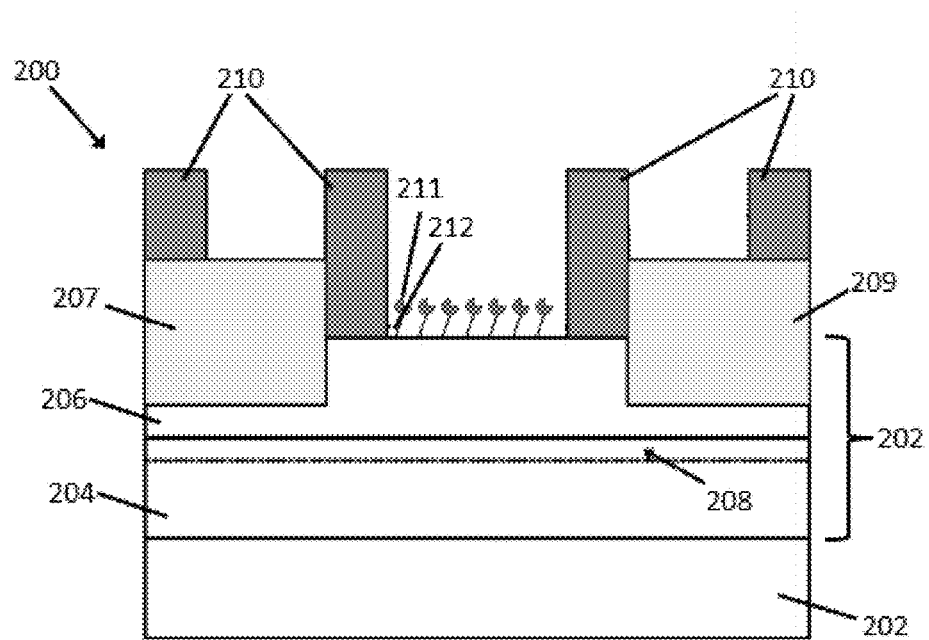
FIG. 2 is a cross-sectional side view of a sensor which includes a channel that comprises a Group III-nitride heterojunction.

An exemplary FET-based sensor is illustrated in FIG. 2. The sensor (200) comprises a substrate (202) and a channel comprising a Group III-nitride heterojunction (202) disposed on the substrate. The Group III-nitride heterojunction (202) comprises a first Group III-nitride layer (204) and a second Group II-nitride layer (206). The first Group III-nitride layer (204) and the second Group III-nitride layer (206) have different bandgaps, such that a two-dimensional electron gas (208) is generated inside the Group III-nitride heterojunction (202). The sensor further includes a source electrode (207) and a drain electrode (209) electrically connected to the Group III-nitride heterojunction (202). The source electrode (207) and the drain electrode (209) are formed to be separate such that the Group III-nitride heterojunction (202) forms a path for current flow between the source electrode (207) and the drain electrode (209). The sensor also includes a recognition element (211) for an analyte of interest immobilized on the surface of the Group III-nitride heterojunction (202) via a linking group (212). An insulator (210) is disposed on the source electrode (207), the drain electrode (209) and the Group III-nitride heterojunction (202) to permit a conductive fluid to be applied to the surface of the Group III-nitride heterojunction (202) without the conductive fluid completing a circuit between the source electrode (207) and the drain electrode (209).

The sensors described herein can be used to rapidly and accurately detect an analyte in physiological conditions. As used herein, the term "physiological conditions" refers to temperature, pH, ions, ionic strength, viscosity, and like biochemical parameters which exist extracellularly or intracellularly in an organism. In some embodiments, the physiological condition refers to conditions found in serum and/or blood of an organism. In some embodiments, the physiological condition refers conditions found in a cell in an organism.

Particular in vitro conditions to mimic physiological conditions can be selected by the practitioner according to conventional methods. For general guidance, the following buffered aqueous conditions can be applicable: 10-250 mM NaCl, 5-50 mM Tris HCl, pH 5-8, with optional addition of divalent cation(s) and/or metal chelators and/or nonionic detergents and/or membrane fractions and/or antifoam agents and/or scintillants. In general, in vitro conditions that mimic physiological conditions comprise 50-200 mM NaCl or KCl, pH 6.5-8.5, 20-45° C., and 0.001-10 mM divalent cation (e.g., $Mg^{2+}$, $Ca^{2+}$); preferably about 150 mM NaCl or KCl, pH 7.2-7.6, 5 mM divalent cation.

Methods for detecting an analyte of interest can include contacting the analyte of interest with a sensor, and measuring a change in an electrical property of the sensor channel. The change in electrical property can be, for example, a change in current flow, a change in voltage, a change in impedance, or combinations thereof.

In some cases, the methods can further include applying a gate bias to the channel. The gate bias can be applied using a gate electrode positioned beneath the channel (i.e., a back gate), adjacent to the channel (e.g., a side gate), or in contact with a conductive fluid contacting the channel surface (e.g., a floating electrode). The gate bias can be selected to allow the sensor to operate in the subthreshold regime. This can allow the sensor to be more sensitive to interaction of the recognition element with the analyte of interest.

The methods described herein can be used to detect analytes in solution. In some embodiments, the analyte of interest is present in an aqueous solution.

The analyte of interest can be present in a biological sample. "Biological sample," as used herein, refers to a sample obtained from or within a biological subject, including samples of biological tissue or fluid origin obtained in vivo or in vitro. Such samples can be, but are not limited to, bodily fluid, organs, tissues (e.g., including resected tissue), fractions and cells isolated from mammals including, humans. Biological samples also may include sections of the biological sample including tissues (e.g., sectional portions of an organ or tissue). The term "biological sample" also includes lysates, homogenates, and extracts of biological samples.

In certain embodiments, the analyte of interest is present in a bodily fluid. "Bodily fluid", as used herein, refers to a fluid composition obtained from or located within a human or animal subject. Bodily fluids include, but are not limited to, urine, whole blood, blood plasma, serum, tears, semen, saliva, sputum, exhaled breath, nasal secretions, pharyngeal exudates, bronchoalveolar lavage, tracheal aspirations, interstitial fluid, lymph fluid, meningal fluid, amniotic fluid, glandular fluid, feces, perspiration, mucous, vaginal or urethral secretion, cerebrospinal fluid, and transdermal exudate. Bodily fluid also includes experimentally separated fractions of all of the preceding solutions, as well as mixtures containing homogenized solid material, such as feces, tissues, and biopsy samples.

The methods described herein can be used to detect an analyte of interest in vivo (i.e., the analyte of interest is contacted with the sensor in vivo). In these instances, methods for detecting an analyte of interest can include advancing a sensor into a patient, contacting the analyte of interest within the patient with the sensor, and measuring a change in an electrical property of the sensor channel.

The methods described herein can be used to detect an analyte of interest ex vivo (i.e., the analyte of interest is contacted with the sensor ex vivo). The term "ex vivo," as used herein, refers to an environment outside of a subject. Accordingly, a sample of bodily fluid collected from a subject is an ex vivo sample of bodily fluid. In these instances, methods for detecting an analyte of interest can include collecting a biological sample from a patient, contacting the analyte of interest in the biological with a sensor, and measuring a change in an electrical property of the sensor channel. In certain embodiments, the ex vivo sample is a biological fluid, lysate, homogenate, or extract.

The methods described herein can be used to detect an analyte of interest in vitro (i.e., the analyte of interest is contacted with the sensor in vitro). Such methods can be used, for example, to monitor tissue cultures.

The analyte of interest can be present in an environmental sample, such as a water sample or soil leachate.

The methods can be used to determine a presence of the analyte of interest, to determine the concentration of the analyte of interest, or a combination thereof.

The sensors and methods described herein can be used to detect a variety of analytes. In order to be detected by the FET-based sensor, the analyte of interest must generate an electric field in proximity to the channel surface. In some cases, the analyte is charged (e.g., the analyte has a net negative or a net positive charge). In other embodiments, the analyte of interest has a net neutral charge, but contains one or more charged regions such that when associated with the recognition element, an electric field is generated which modulates the electronic properties of the channel.

The analyte of interest can comprise a macromolecule, such as a biomacromolecule. "Macromolecule," as used herein, refers to a large molecule, typically having a high relative molecular weight, such as a polymer, polysaccharide, protein, peptide, or nucleic acid. The macromolecule can be naturally occurring (i.e., a biomacromolecule) or can be prepared synthetically or semi-synthetically. In certain embodiments, macromolecules have a molecular weight of greater than about 1000 amu (e.g., greater than about 1500 amu, or greater than about 2000 amu).

In some embodiments, the analyte of interest is an antibody, peptide (natural, modified, or chemically synthesized), protein (e.g., glycoproteins, lipoproteins, or recombinant proteins), polynucleotide (e.g, DNA or RNA), lipid, polysaccharide, pathogen (e.g., bacteria, virus, or fungi, or protozoa), or a combination thereof. In certain embodiments, the analyte of interest comprises a biomarker for a disease process in a patient.

The sensors can be used in place of existing immunoassays, such as ELISAs, in clinical and research settings to detect proteins and peptides and/or to measure the concentration of proteins and peptides. For example, the sensors can be used to detect antibodies or antigens in a sample.

The sensors can be used in clinical and healthcare settings to detect biomarkers (i.e., molecular indicators associated with a particular pathological or physiological state). The sensors can be used to diagnose infections in a patient (e.g., by measuring serum antibody concentrations or detecting antigens). For example, the sensors can be used to diagnose viral infections (e.g., HIV, hepatitis B, hepatitis C, rotavirus, influenza, or West Nile Virus), bacterial infections (e.g., *E. coli*, Lyme disease, or *H. pylori*), and parasitic infections (e.g., toxoplasmosis, Chagas disease, or malaria). The sensors can be used to rapidly screen donated blood for evidence of viral contamination by HIV, hepatitis C, hepatitis B, and HTLV-1 and -2. The sensors can also be used to measure hormone levels. For example, the sensors can be used to measure levels of human chorionic gonadotropin (hCG) (as a test for pregnancy), Luteinizing Hormone (LH) (to determine the time of ovulation), or Thyroid Stimulating Hormone (TSH) (to assess thyroid function). The sensors can be used to diagnose or monitor diabetes in a patient, for example, by measuring levels of glycosylated hemoglobin, insulin, or combinations thereof. The sensors can be used to detect protein modifications (e.g., based on a differential charge between the native and modified protein and/or by utilizing recognition elements specific for either the native or modified protein).

The sensors described herein can also be used, for example, to detect and/or monitor the levels of therapeutic peptides in vivo. For example, the sensors can be used to detect and/or monitor the levels of growth hormone, interferon-alpha, rituximab, infliximab, etanercept, or bevacizumab in vivo. This could be used during treatment (e.g., to titrate clinically preferred levels of a therapeutic peptide) as well as during clinical trials.

The sensors can be used to detect proteinaceous toxins, including mycotoxins, venoms, bacterial endotoxins and exotoxins, and cyanotoxins. For example, the sensors could be used to detect botulinum toxin, ricin, tetanus toxin, *C. difficile* toxin A, *C. difficile* toxin B, or staphylococcal enterotoxin B (SEB).

The sensors can also be used in other commercial applications. For example, the sensors can be used in the food industry to detect potential food allergens, such as milk, peanuts, walnuts, almonds, and eggs. The sensors can be used to detect and/or measure the levels of proteins of interest in foods, cosmetics, nutraceuticals, pharmaceuticals, and other consumer products.

The sensors can be used in the biotechnology industry to measure the concentration of biomolecules, such as antibodies, during manufacture.

The sensors described herein can be integrated into devices to facilitate the detection of analytes in vivo, ex vivo, and in vitro. For example, the sensors described herein can be integrated into a variety of existing medical devices, research instruments, and vessels (e.g., micro-well plates) to provide a real-time capability for rapidly and accurately assaying the presence of one or more analytes of interest.

Figure 3:
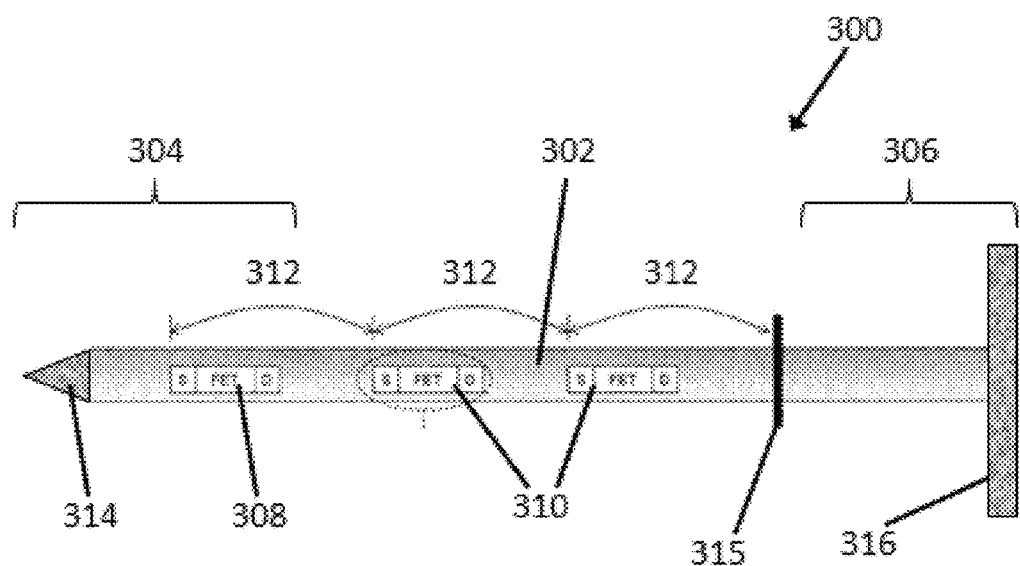
FIG. 3 is a side view of a probe containing one or more sensors.

By way of exemplification, the sensors described herein can be integrated into probes that can be utilized to detect analytes of interest in vivo or in vitro. An example probe is illustrated in FIG. 3. The probe (300) comprises an elongate member (302) having a proximal end (306) and a distal end (304), and one or more sensors (308) positioned at the distal end of the elongate member. The one or more sensors (308) can comprise recognition elements that selectively associate with the analyte of interest.

The dimensions of the elongate member can be varied based on the intended application of the device. Generally, the length of the elongate member can be selected to facilitate storage and deployment of the probe in conjunction with the desired sensing application.

For example, in some embodiments, the probe can be placed in contact with cells, cell aggregates, or tissue samples to detect analytes of interest. In these cases, the dimensions of elongate member (e.g., length and diameter or thickness) can be appropriately sized to contact cells or cell aggregates (e.g., less than 0.5 mm in length, or less than 500 microns in length).

In other embodiments, the probe can be used to measure an analyte, such as a biomarker, in a patient. In these embodiments, the dimensions of the elongate member can be selected to facilitate interrogation of the patient. For example, in some embodiments, probes may be used to interrogate fluids and/or tissues within a patient to detect biomarkers diagnostic of a disease process. In these instances, the dimensions of the probe may be varied, for example based on the location of the fluids and/or tissues within the patient. Similar probes can also be used to detect analytes ex vivo or in vitro (i.e., a dipstick assay).

In some embodiments, the elongate member has a length of at least about 0.5 cm (e.g., at least about 1 cm, at least about 2 cm, at least about 3 cm, at least about 4 cm, at least about 5 cm, at least about 6 cm, at least about 7 cm, at least about 8 cm, at least about 9 cm, at least about 10 cm, at least about 11 cm, at least about 12 cm, at least about 13 cm, at least 14 cm, at least about 15 cm, at least about 16 cm, at least about 17 cm, at least about 18 cm, at least about 19 cm, at least about 20 cm, at least about 21 cm, at least about 22 cm, at least about 23 cm, at least about 24 cm, at least about 25 cm, at least about 26 cm, at least about 27 cm, at least about 28 cm, at least about 29 cm, or longer. In some embodiments, the elongate member has a length of less than about 30 cm (e.g., less than about 25 cm, less than about 20 cm, less than about 19 cm, less than about 18 cm, less than about 17 cm, less than about 16 cm, less than about 15 cm, less than about 14 cm, less than about 13 cm, less than about 12 cm, or less than about 11 cm). The length of the elongate member can optionally range from any of the minimum dimensions described above to any of the maximum dimensions described above.

In some cases, the largest cross-sectional dimension of the elongate member is about 5.0 mm or less (e.g., about 4.5 mm or less, about 4 mm or less, about 3.5 mm or less, about 3 mm or less, about 2.5 mm or less, about 2 mm or less, about 1.5 mm or less, or about 1.0 mm or less). The largest cross-sectional dimension of the elongate member can be at least about 0.2 mm (e.g., at least about 1.0 mm, at least about 1.0 mm, at least about 1.5 mm, at least about 2.0 mm, at least about 2.5 mm, or at least about 3.0 mm). The largest cross-sectional dimension of the elongate member can optionally range from any of the minimum dimensions described above to any of the maximum dimensions described above. These dimensions are provided with the proviso that the cross-sectional dimensions and composition of the elongate member are selected such that the structural integrity of the elongate member required for probe function is not substantially compromised by the cross-sectional dimension of the elongate member.

The elongate member can be substantially cylindrical in shape. In some embodiments, the elongate member is a wire-like structure a cross-sectional dimension, length, and flexibility suitable to assist in insertion of the probe into the tissue of a patient and/or the probe's subsequent removal from the tissue of a patient.

The elongate member can be flexible or rigid, depending on the intending application of the device. In some cases, at least a portion of the elongate member is flexible. In some instances, the elongate member is flexible along its entire length. In other embodiments, the elongate member comprises two or more regions having different flexibility. In certain embodiments, the elongate member comprises a flexible region located at or near the distal end of the elongate member, and a region having greater rigidity than the flexible region (referred to as a rigid region) located at or near the proximal end of the elongate member.

The elongate member, or a flexible region thereof, can have a flexural stiffness of less than about 500 pounds-force per inch over an elongate member length of one inch (e.g., less than about 400, less than about 300, less than about 250, less than about 200, or less than about 100 pounds-force per inch over an elongate member length of one inch). In certain embodiments, the elongate member, or a region thereof, can be bent without fracture to angle of greater than 30° (e.g., to an angle of greater than 45°, greater than 60°, greater than 70°, greater than 90°, greater than 120°, greater than 135°, greater than 150°, or greater than 180°).

The elongate member, or regions thereof, can be formed from a variety of materials, such as polymers, metals, and polymer-metal composites. In some cases when the probe is to be used within a patient, soft durometer materials are used to form all or part of the elongate member to reduce patient discomfort and/or minimize trauma to tissue. Examples of suitable metals include stainless steel (e.g., 304 stainless steel), nickel and nickel alloys (e.g., nitinol or MP-35N), titanium, titanium alloys, and cobalt alloys. Examples of suitable plastics and polymeric materials include, but are not limited to, silastic materials and siliconbased polymers, polyether block amides (e.g., PEBAX®, commercially available from Arkema, Colombes, France), polyimides, polyurethanes, polyamides (e.g., Nylon 6,6), polyvinylchlorides, polyesters (e.g., HYTREL®, commercially available from DuPont, Wilmington, Del.), polyethylenes (PE), polyether ether ketone (PEEK), fluoropolymers such as polytetrafluoroethylene (PTFE), perfluoroalkoxy, fluorinated ethylene propylene, or blends and copolymers thereof. In certain embodiments, the elongate member comprises of two different materials. For example, the elongate member may be formed of a flexible material forming a flexible region of the elongate member and a semi-rigid or rigid material forming a rigid region of the elongate member. In other cases, the elongate member, or region thereof, is formed from a combination of a semi-rigid internal material and a soft, pliable exterior material. Radiopaque alloys, such as platinum and titanium alloys, may also be used to fabricate, in whole or in part, the elongate member to facilitate real-time imaging of probe positioning.

The elongate member can be coated or treated with various polymers or other compounds in order to provide desired handling or performance characteristics, such as to increase lubricity. In certain embodiments, the elongate member is coated with polytetrafluoroethylene (PTFE) or a hydrophilic polymer coating, such as poly(caprolactone), to enhance lubricity and impart desirable handling characteristics.

In some cases, the elongate member is straight (i.e., unbent) when no force is applied to the elongate member. In other cases, one or more preformed bends or curves can be incorporated into the elongate member to facilitate deployment of the device in vivo.

Referring again to FIG. 3, the probe (300) can optionally include one or more additional sensors (310) positioned along the length of the elongate member (302) between the proximal end (306) and the distal end (304). The one or more additional sensors (310) can be positioned at known intervals (312) along the length of the elongate member. In some cases, each of the known intervals (312) are substantially equivalent in length.

The probe can optionally include a plurality of the sensors positioned radially around the longitudinal axis of the elongate member. In one embodiment, at each point or interval along the elongate member where sensors are positioned, a plurality of the sensors positioned radially around the longitudinal axis of the elongate member.

In one embodiment, the probe is configured with the sensors appended at known positions on its surfaces, such that upon insertion into tissue, the sensors are exposed to analytes present in tissue or tissue fluid. Because the position of the sensors on the probe surface are known, the concentration of analytes as a function of sensor position in the tissue can be determined, and potentially, mapped over time or as a function of position in tissue.

Referring again to FIG. 3, the probe can further include a ridge (315) located along the elongate member (315). The ridge can function as a guide for the device user to facilitate proper placement of the probe within a sample (e.g., as a stop point or depth indicator). The probe can optionally include a tapered or pointed distal tip (314) to facilitate insertion of the probe into, for example, tissue. If desired, an actuating element (316) can be affixed to the proximal end (306) of the elongate member (302). The actuating element can be a surface or feature, such as a handle, ring, nob, or flange, which is configured to facilitate actuation of the probe (e.g., to facilitate a physician in positioning the probe within a patient).

As discussed above, the probes described herein can be used to detect an analyte, such as a biomarker, in a patient. The probes can be packaged in kits for use in primary care settings in combination with instructions for use. The probes can also be packed in kits for sale in a pharmacy in combination with instructions for use. The probes can provide a point-of-care means of rapidly diagnosing disease processes, such as infections. Preferably, they allow a clinician to receive critical information regarding a disease process, for example, in the clinic or at the patient's bedside as opposed to having to wait hours or days to receive immunoassay results from a laboratory.

Unlike conventional immunoassays, such as ELISA, the probes can be used to detect biomarkers in situ within a patient. As a consequence, biomarkers can be detected in tissue without requiring the tissue to be removed, obviating tissue trauma (along with the morbidity associated with, for example, tissue biopsy).

By way of exemplification, the probes described herein can be used to detect the levels of biomarkers in tissue, for example, grafted tissue to monitor a graft recipient for a rejection response. "Graft" and "Grafted tissue," as used herein, refer to cells or tissue in the body of a recipient mammal which are implanted from another individual of the same species (allograft) or from a different species (xenograft). In some embodiments, the grafted tissue can be lung tissue, heart tissue, liver tissue, kidney tissue, intestinal tissue, or pancreatic tissue.

Graft rejection occurs when grafted tissue is rejected by the recipient's immune system, which destroys the graft tissue. Biomarkers of graft rejection are known in the art and include, for example, monokine induced by interferon γ (MIG), interferon gamma-induced protein 10 (IP-10), chemokine (C-C motif) ligand 5 (CCL5).

Probes and sensors containing recognition elements that selectively associate with a biomarker for graft rejection, such as MIG, IP-10, and/or CCL5, can be used to monitor a graft recipient for a rejection response. The probes and sensors can be inserted into grafted tissue or into fluid adjacent to grafted tissue. Biomarkers for graft rejection can then be detected in the tissue by measuring a change in an electrical property of the sensor(s) in the probe. A therapeutic regimen can be administered to the graft recipient in view of the biomarker detected in the graft. For example, an immunosuppressant regime can be commenced or altered.

Also provided are multi-well plates which include sensors deployed in one or more of the wells of the microwell plates. Multi-well plates can include a base comprising a first material having a substantially co-planar top and bottom surface, a plurality of microwells disposed in the base, wherein each microwell comprises a solid bottom proximal to the bottom surface of the base, one or more solid side walls, and an opening located on the top surface of the base, and a sensor positioned within one or more of the plurality of microwells. The one or more sensors are configured such that the recognition element of the sensor is in contact with the contents of the microwell in which it is positioned.

In some embodiments, the multi-well plate is configured to have dimensions, including well diameter, well spacing, well depth, well placement, plate dimensions, plate rigidity, and combinations thereof, equivalent to the standard dimensions for microwell plates published by the American National Standards Institute (ANSI) on behalf of the Society for Biomolecular Sciences (SBS). See, for example, Journal of Biomolecular Screening. Vol 1, Number 4, 1996, pp. 163-168, which is incorporated herein by reference for its description of the standard dimensions of multi-well plates. In this way, the multi-well plate can be rendered compatible with existing technologies for plastic MICROTITER® plates, including 8-channel micropipettes and automated plate readers.

The multi-well plates can be fabricated from any suitable material, such as a plastic (e.g., polystyrene, polypropylene, or a cyclic olefin copolymer) The multi-well plate can contain any number of microwells, as desired for a particular application. In some embodiments, the multi-well plate can comprise from 6 to 10,000 microwells (e.g., from 6 to 384 microwells). In some embodiments, the microwells in the multi-well plate are arranged in a 2:3 rectangular matrix. In certain embodiments, the multi-well place comprises 6, 24, 96, 384, 1536, 3456, or 9600 microwells.

Figure 4A:
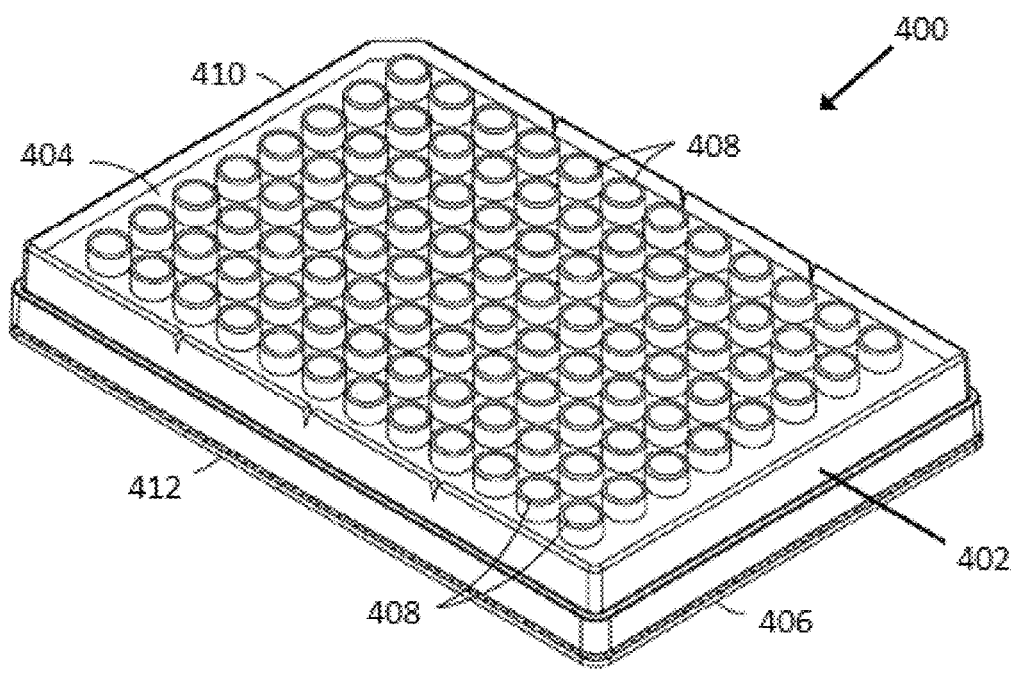
FIG. 4A is a perspective view of a multi-well plate.

Referring now to FIG. 4A, the multi-well plate (400) can include a base (402) having a substantially co-planar top (404) and bottom (406) surface. A plurality of microwells (408) are disposed in the base (402). The multi-well plate can optionally include a rim (410) or a lip (412) located around the top or bottom surface of the base to facilitate compatibility of the device with automated plate readers and lids.

Figure 4B:
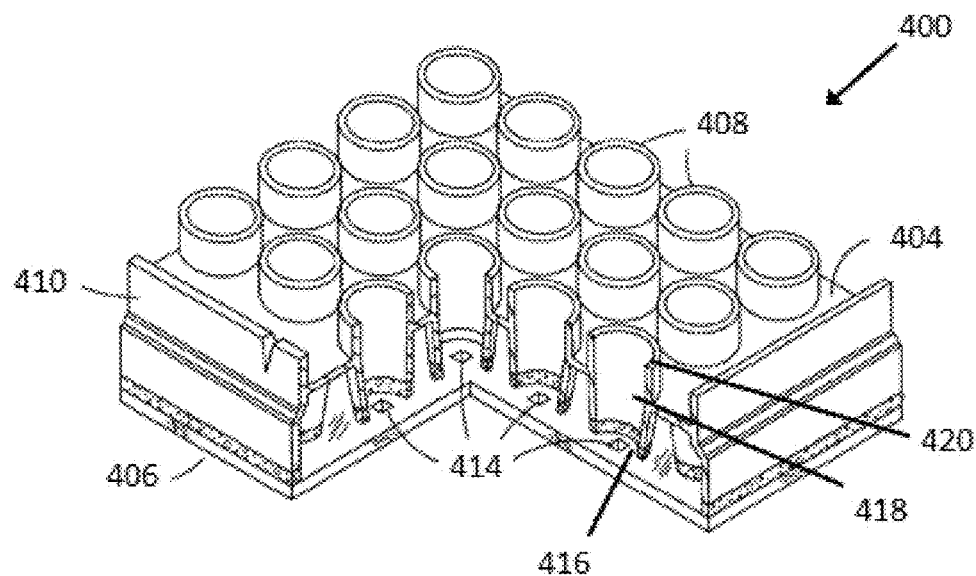
FIG. 4B is an enlarged cross-sectional view of a portion of the multi-well plate illustrated in FIG. 4A.

Referring now to FIG. 4B, each of the microwells (408) has a solid bottom (416) proximal to the bottom surface of the base (406), one or more solid side walls (418), and an opening (420) located on the top surface of the base (404). A sensor (414) is positioned within one or more of the microwells (408). The sensors (414) are configured such that the recognition element of the sensor is in contact with the contents of the microwell in which it is positioned.

In certain embodiment, a sensor is positioned within each of the plurality of microwells in the multi-well plate. In other embodiments, one or more microwells in the multi-plate do not contain sensors. For example, certain regions of the plate can contain microwells which are reserved for other assays to be conducted in parallel with analyte detection using the FET-based sensors.

In some embodiments, each sensor in the multi-well plate comprises a recognition element for a different analyte of interest. In this way, array-type sensor plates can be generated, for example, to screen samples for a variety of analytes of interest simultaneously. In some embodiments, each sensor in the multi-well plate comprises a recognition element for the same analyte of interest. In this way, a screening plate for a single analyte of interest can be generated, for example, to simultaneously screen samples from a number of sources for a single analyte of interest.

Also provided are kits for the preparation of the sensors, probes, and micro-well plates described herein. Kits can include a sensor precursor comprising a substrate, a channel (e.g., a Group III-nitride heterojunction) disposed on the substrate, and a source electrode and a drain electrode electrically connected to the channel, wherein the source electrode and the drain electrode are formed to be separate such that the channel forms a channel for current flow between the source electrode and the drain electrode.

In some embodiments, the kit includes a sensor precursor, a recognition element for an analyte of interest, and a linker comprising a first reactive moiety and a second reactive moiety, wherein the first reactive moiety is reactive with the channel and the second reactive moiety is reactive with the recognition element. The kit can further include instructions for functionalizing the channel surface using the recognition element and the linker.

In other embodiments, the kit includes a sensor precursor, and a linker comprising a first reactive moiety and a second reactive moiety, wherein the first reactive moiety is reactive with the channel. The kit can further include instructions for selecting recognition element for an analyte of interest which is reactive with the second reactive moiety, and functionalizing the channel surface using the recognition element and the linker. In this way, researchers can use these kits to prepare sensors, probes, and multi-well plates having customized recognition elements.

In other cases, the sensor precursor can comprise a substrate, a channel (e.g., a Group III-nitride heterojunction) disposed on the substrate, and a source electrode and a drain electrode electrically connected to the channel, wherein the source electrode and the drain electrode are formed to be separate such that the channel forms a channel for current flow between the source electrode and the drain electrode, and a linker disposed on the surface of the channel, wherein the linker contains a reactive moiety. These sensor precursors can be sold in a kit, which can further include instructions for selecting a recognition element for an analyte of interest which is reactive with the reactive moiety of the linker, and functionalizing the channel surface using the recognition element. The kit can optionally further include a recognition element for the analyte of interest.

EXAMPLES

Example 1

Detection of Analytes in Physiological Salt Environments

Biosensing modalities can be of pivotal utility in clinical settings. Biosensors detecting appropriate analytes, with sensitivities and modes of operation, can potentially detect incipient disease prior to manifestation of clinical symptoms, reducing patient morbidity and mitigating mortality. Optimally, such sensors should operate non- or minimally invasively, such that the act of sensing itself does not impose significant morbidity on the patient.

Electrochemical biosensors couple a recognition element (e.g., a receptor that binds to a specific analyte of interest with high affinity) with a transducer element to convert a biological event (e.g., binding of analyte to recognition element, production of an enzymatic reaction product, consumption of an enzyme substrate, etc.) into an electrically measurable signal. This general paradigm has been manifest in electrochemical biosensors since the earliest attempts to sense biologically important small molecules or macromolecules, and was followed in the first electrochemical biosensor (the glucose enzyme electrode).

The glucose enzyme electrode was followed by the development of the earliest ion selective field-effect transistors (ISFETs). ISFET design was significantly refined within a decade of inception of the sensing modality. ISFETs feature integration of bioaffinity/catalytic elements (in ISFETs, typically an enzyme) deployed in the place of a gate on the capacitance layer of a metal oxide semiconductor field-effect transistor (MOSFET). Basic ISFET operation is broadly similar to operation of conventional FETs, excepting that ISFET current modulation is provided by ions produced by the enzyme and not by an electrical bias on a gate electrode. This coupling of biological affinity elements (receptors, antibodies, other proteinaceous affinity elements, nucleic acids of various descriptions, etc.) with the field-effect modulation principle of semiconductor devices was enticing, offering the promise of rapid, highly sensitive detection using a sensing platform (i.e., the MOSFET) that had been highly developed in the electronics industry. The ability of ISFETs to detect ionic charges led some to consider the possibility that charged analytes, including biological macromolecules (e.g. proteins, nucleic acids), might also be detectable by FETs.

The measurement of proteins via their intrinsic charges was first proposed by Schenk when he envisioned deploying a receptor layer of antibodies with specific affinity for an antigen of interest (i.e., a protein analyte) on the gate region of a FET (i.e., an immunoFET). One of the earliest immunoFET-like sensors featured immobilized anti-human serum albumin (anti-HSA) IgG on a polyvinylbutyral (PVB) membrane overlying an ISFET-sensing channel. These experiments demonstrated that proteins could potentially be detected via immunoFET: however, these devices were not able to reproducibly detect and/or quantify analytes at physiological salt concentrations (~150 mM $Na^+$).

On their face, immunoFETs would seem an ideal platform for label-free protein detection. However, direct sensing of immunoconjugation events by FET has proven challenging. Charges on analytes can be shielded from the surface of the FET sensing channel by buffer ions, reducing the magnitude of bound analyte signal. The distance over which this shielding electrical layer of buffer ions forms (the Debye length) is 1-2 nm at physiological salt concentrations (~150 mM $Na^+$). This shielding layer is believed to completely screen the electrical field of uniformly charged surfaces. When considered in the context of ImmunoFET function, this argument is applied to the shielding of protein electrical charges by buffer counterions. This Debye length limitation is often considered "fundamental" for FET sensing of protein-protein interaction, purportedly rendering immunoFET protein detection infeasible in physiological buffer.

For example, in a classical analysis by Bergveld, immunoFET sensing was labeled as infeasible for in vivo applications because antibodies on the surface of the FET would hold the analyte too far from the surface to allow reliable detection. See, for example Bergveld, P. *Biosensors and Bioelectronics,* 6(1):55-72(1991). Intact IgG is approximately 10-12 nm in length. Thus, if one bound the antibody by its C3 domain to a FET sensing surface, the variable region (site of analyte binding) would extend well beyond the Debye length at physiological ion concentrations. One would expect that the charges on bound analytes would be shielded by the electrical double layer and therefore be undetectable. This analysis has taken hold as dogma in the FET-sensing field, and it has long been considered impossible to utilize immunoFETs to detect analytes in physiological conditions.

However, this classical reasoning is immunologically unsound for multiple reasons. For classical analysis to be valid, antibodies must (i) be rigid bodies that (ii) adsorb to the sensing surface solely through their terminal C3 domain. Logically, failure of antibodies to conform to either of these conditions calls classical analysis into question. In fact, antibodies adsorb to surfaces via a nearly random distribution of their structural domains. Moreover, antibodies are highly flexible, able to bend through arcs of 180° or more, with additional flexibility provided by the so-called 'molecular ball and socket' region occurring between the V and C1 domains.

The combination of antibody adsorption in variable orientations relative to the surface and antibody flexibility causes bound analytes to be held in a distribution of orientations and distances from the sensing surface. Some of the analyte charges should thus be expected to be held within the Debye length, and therefore analyte electrical fields should be detectable by FETs. That antibody adsorption to surfaces is not typically oriented, and that antibodies are indeed highly flexible, is not only immunological orthodoxy but also provides a rationale for successful immuno- and bioFETs. These facts also indicate that, when immunoFETs fail, the mechanism is probably not as described by the classical model. This is important because understanding the mode of failure can potentially drive remediation of the immunoFET design.

Classical assessment further ignores potential interfacial design approaches to minimize the distance between bound analyte charges and immunoFET sensing surfaces to maximize sensitivity. Neither does classical assessment consider differentiable ion permeability of various FET platforms. Ion permeation alters electrical properties of MOSFETs, impeding accurate sensing. Less ion permeable FETs (e.g., AlGaN/GaN HFETs) offer the potential to reduce the impact of ion permeability on sensor signal (e.g., current, voltage, conductance, or impedance) drift.

Through careful sensor design, multiple functional immunoFETs were prepared and used to detect analytes in physiological buffers, contrary to predictions of classical analysis. For purposes of demonstration, monokine induced by interferon-g (MIG, CXCL9) of humans and mice was selected as an analyte. In both species, MIG is a pro-inflammatory chemokine that is a chemoattractant for cytotoxic T-cells. MIG increases during inflammatory responses, rising from a normal concentration of 40-100 pM, to 1-2 orders of magnitude higher during acute inflammation. In transplant biology, rising graft MIG concentrations precede allograft rejection and can be used as an early indicator of imminent rejection. Human and murine MIG (huMIG, muMIG) have about 80 percent protein sequence identity, similar isoelectric points and perform similar physiological functions, but are immunologically differentiable. Antibodies (IgG) specific for huMIG and muMIG were used to build species-selective immunoHFETs.

Materials and Methods

Chemicals and Reagents

Triethoxysilane aldehyde (TEA) was obtained from United Chemical Technologies (Bristol, Pa.). Aminopropyl triethoxysilane (APTES) was purchased from Gelest, Inc. (Morrisville, Pa.). Polyclonal anti-muMIG IgG was purchased from R&D Systems, Inc. (Minneapolis, Minn.). Polyclonal anti-huMIG IgG, biotinylated anti-huMIG IgG and recombinant huMIG and muMIG were purchased from Peprotech. Inc. (Rocky Hill, N.J.). EZ-Link Sulfo-NHS biotin was purchased from Pierce, Inc. (Rockford, Ill.). Streptavidin (SA), SA conjugated to horseradish peroxidase (SA-HRP), and Dulbecco's phosphate-buffered saline (PBS) containing 150 mM NaCl, pH 7.4, were purchased from Invitrogen. Inc. (Carlsbad, Calif.). o-phenylenediamine dihydrochloride (OPD) tablets were purchased from Sigma-Aldrich, Co. (St. Louis, Mo.). All commercially available materials were used without further purification, unless otherwise stated below.

Transistor Fabrication

AlGaN/GaN HFETs were constructed using previously described methodologies. AlGaN/GaN heterostructures were purchased from CREE, Inc. (Raleigh, N.C.), and surface oxidized via inductively-coupled plasma treatment (ICP) by oxygen plasma. About 15 nanometers of the AlGaN barrier was recessed in a Cl-based ICP plasma so that the threshold voltage of the device was shifted to the −0.5 to +0.5V range. The conducting channel of the HFETs varied from 50 to 100 µm in width and length. The device reservoir with an average height of 10-20 µm allowed the conducting channel access by the samples. The chemical gate formed on the oxide was functionalized with receptors (antibodies or SA) for specific analyte binding.

Surface Preparation and Device Sample Exposure

For the huMIG and muMIG receptor-specificity experiments, AlGaN HFETs were surface functionalized with 5 percent TEA in ethanol (following the APTES deposition protocol) and subsequently 1 µgml-1 anti-huMIG or anti-muMIG IgGs. The sample reservoir was exposed to 15 ml of 5 mgml-1 (0.43, 0.41 mM, respectively) huMIG or muMIG.

For experiments comparing detection of mixed biotinylated and native MIG samples (bMIG and huMIG, respectively), two AlGaN HFETs were used. One device was functionalized with 5% APTES by weight in ethanol, biotinylated using 1 mg ml$^{-1}$ biotin at 37° C., and subsequently treated with 5 µg ml$^{-1}$ SA. This device was used for bMIG detection using SA as the specific recognition element to bind biotin on bMIG. The second device was functionalized as described above with 5% by weight TEA in ethanol and anti-huMIG IgG and used to detect MIG (both MIG and bMIG).

Electrical Measurements

Three-terminal (source, drain and gate) current-voltage characteristics of AlGaN/GaN HFETs were measured using an Agilent 4156C semiconductor parameter analyser at room temperature. The gate bias was biased through a reference electrode floating in the solution. The source/drain current was modulated by the gate bias to the order of 1 µA mm$^{-1}$ for detections, so that the device is working in the subthreshold regime for best device performance. A device source/drain characteristic was first measured with PBS only (baseline measurement). The protein solution was then applied with a micro-pipette and incubated for 5 minutes, after which second source/drain characteristics were measured for comparison. The charges introduced by the binding of analyte to surface receptors modulate the source/drain current.

Immunosorbent Assay

ELISAs were performed in 96-well Nunc Maxisorb ELISA plates to corroborate electrical sensor data. For huMIG versus muMIG detection, wells were incubated with 1 µg ml$^{-1}$ anti-huMIG or anti-muMIG IgG for 1 hour at 37° C.; background wells were incubated with PBS. Wells were then blocked with 5 percent bovine serum albumin (BSA) in PBS for 2 hours at 37° C. before exposure to 10 ng ml$^{-1}$ huMIG or muMIG for 10 minutes at 37° C. Subsequently, wells were incubated with 1 µgml-1 biotinylated anti-huMIG or anti-muMIG IgG for 1 hour at 37° C. Plates were then incubated with 1 µg ml$^{-1}$ SA-HRP in PBS for 1 hour at 37° C. OPD was freshly prepared according to the manufacturer's directions and added to each well for 20 minutes; the reaction was stopped with 3M $H_2SO_4$, and the absorbance of the reacted OPD solutions were measured in a Victor X3 Plate Reader (spectrophotometer from Perkin-Elmer) at 490 nm. Wells were rinsed five times in 0.1% Tween-20 in PBS between each step.

For confirmation of bMIG/MIG electrical sensing data, ELISAs similar to those described above were performed. In these tests, wells were treated as above with anti-huMIG IgG for MIG detection. Treatment for these tests varied in that the wells were exposed to solutions of bMIG/MIG in varying ratios as opposed to solely huMIG. Wells were also treated for detection of bMIG using SA as the detection agent. Wells were incubated with 500 ng ml$^{-1}$ SA for 2 hours at 37° C. followed by exposure to 1 ng ml-1 bMIG/MIG solutions (0-100% bMIG in 20% increments) for 30 minutes at room temperature. Wells were then incubated in 1 µg ml$^{-1}$ SA-HRP and exposed to OPD as above. Absorbance of reacted OPD solutions for all wells was measured in the Victor X3 Plate Reader at 490 nm.

Figure 5A:
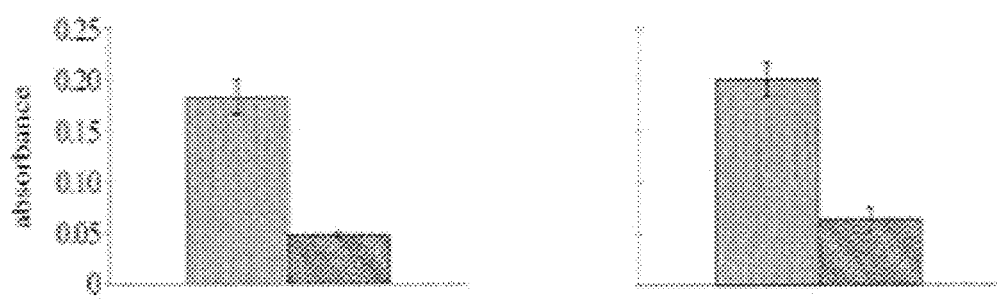
FIGS. 5A-5B illustrate the detection of huMIG and muMIG using ELISA (FIG. 5A) and immune-heterojunction FETs (HFETs) (FIG. 5B). ELISA was used to demonstrate selectivity of antibodies to huMIG (left panel, FIG. 5A) and muMIG (right panel, FIG. 5A). Reactivities of anti-huMIG antibodies with huMIG (left panel, FIG. 5A) and anti-muMIG antibodies with muMIG (right panel, FIG. 5A) are shown by grey bars. Reactivities of anti-huMIG with muMIG (left panel, FIG. 5A) and (b) anti-muMIG with huMIG (right panel, FIG. 5A) are shown by cross-hatched bars. Responses of immunoHFETs with antibodies to huMIG (left panel, FIG. 5B) and antibodies to muMIG (right panel, FIG. 5A) decorating their respective sensing channels to PBS (solid triangles), PBS with 5 μg ml$^{-1}$ huMIG (open squares), and PBS with 5 μg ml$^{-1}$ muMIG (open circles). Current changes associated with species-matched MIG treatment reproduced within 10% (n=3).
Figure 5B:
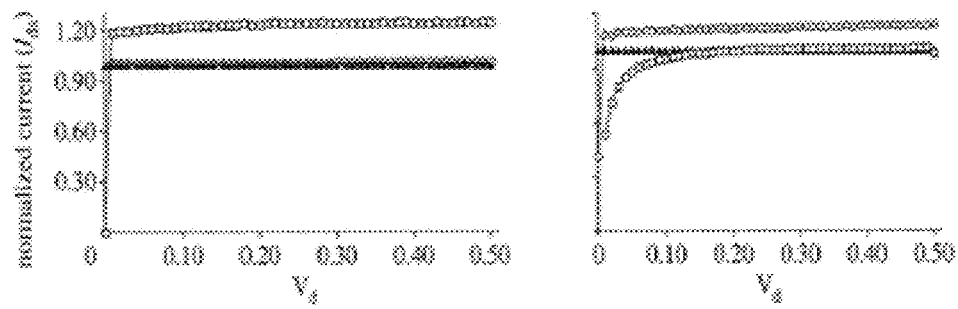

Results and Discussion huMIG and muMIG in PBS were quantified and the species selectivity of anti-huMIG and anti-muMIG IgGs were corroborated by ELISA (FIG. 5A). huMIG and muMIG are positively charged (+19 charges/muMIG, +20 charges/huMIG, pH 7, 4) and HFETs are n-type: their charge carriers are electrons. Therefore, as expected, binding of huMIG or muMIG to sensing channels increased current drain to source ($I_{ds}$; FIG. 5B). However, the immunologically distinct MIG species are detected differentially by immunoHFETs with corresponding species-specific antibodies on their channels (FIG. 5B).

Both murine and human-specific MIG immunoHFETs exhibited unchanged $I_{ds}$ after exposure to PBS. Anti-huMIG immunoHFETs exposed to muMIG gave responses similar to PBS background, and anti-muMIG immunoHFETs exposed to huMIG also gave responses comparable to background. Conversely, immunoHFETs decorated with anti-huMIG IgG exhibited approximately 22% $I_{ds}$ increase upon exposure to huMIG, and sensors with anti-muMIG IgG exposed to muMIG exhibited approximately 15% $I_{ds}$ increase (FIG. 5B). huMIG and muMIG minimal detection limits were similar (approx. 1 fM). Analyte detection specificities of immunoHFETs reflect ELISA-demonstrated antibody-binding specificities (FIG. 5A), though the assays are different (ELISA incorporates multiple secondary reagents that the immunoHFET assay does not).

Having demonstrated that homologous but immunologically distinct analytes are differentially detected by immunoHFET, the ability of immunoFETs to discriminate between immunologically similar but distinct analytes in single samples was evaluated. Native (unbiotinylated) and biotinylated huMIG were mixed at varying stoichiometries and assayed by bioFET (SA as receptor), and immunoFET (antihuMIG IgG as receptor). Neither the bioFET nor the immunoFET responded to PBS, nor did the SA bioFET respond to native MIG. However, immunoHFETs with anti-huMIG on their sensing channels detected huMIG regardless of biotinylation state (reflecting total huMIG, bioinylated and native; FIG. 6B), while streptavidin bioFETs detected only biotinylated analyte, differentially detecting the varying concentrations of biotinylated huMIG in samples (FIGS. 6A and 6B).

Figure 6A:
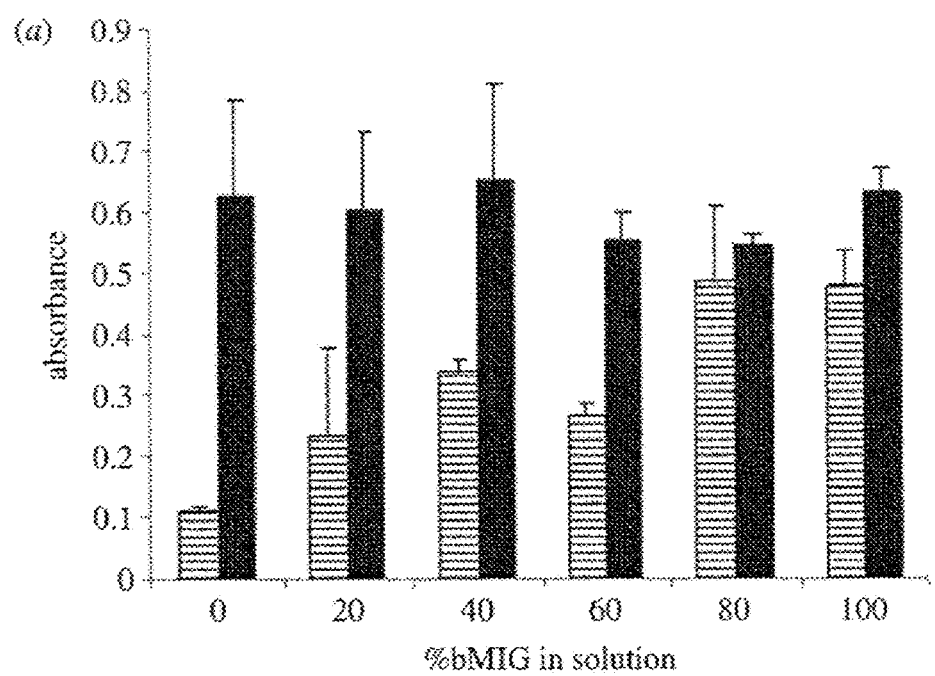
FIGS. 6A-6B illustrate the differential detection of native and biotinylated huMIG in mixed samples by immunoassay (FIG. 6A) and immuno- and bioFET assays (FIG. 6B).
Figure 6B:
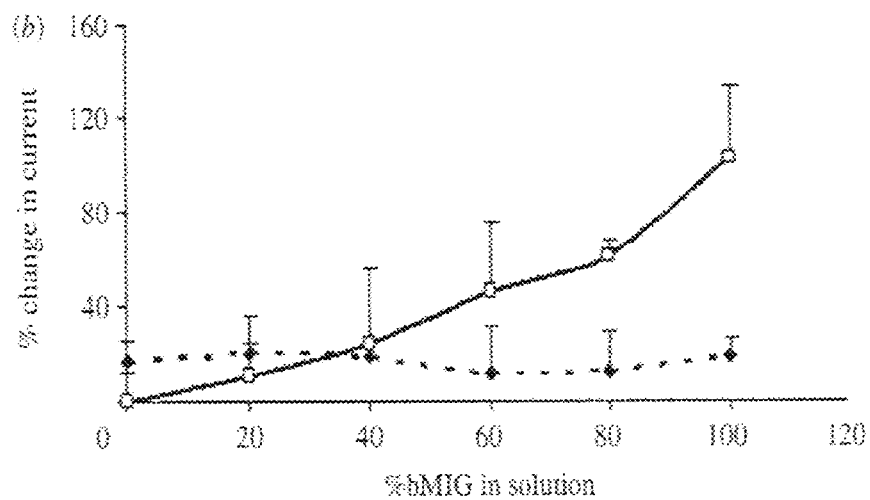

Immuno/bioHFETs detect MIG at biologically meaningful concentrations in physiological buffers and can be configured to detect analyte mixtures, or single constituents of mixtures (FIGS. 6A-6B). These results are contrary to classical assessment that immunoFETs are unable to effectively sense proteins in physiological conditions. This classical assessment was flawed, and failed to model actual behaviour of immunoHFETs because it misrepresents antibody properties. The classical analysis assumes that antibodies are rigid and uniformly oriented on the immunoFET channels (adhering to surfaces solely by C3 domains)

These successful sensing results reflect the invalidity of those assumptions. IgG hinge region (between C2 and C1 domains) flexibility, known since immunoglobulin structure was determined, allows individual arms of antibodies (consisting of C1 and variable domains) to bend through arcs of up to 180°. This conformational freedom is critical to antibody biology. Hinge flexibility allows binding of multivalent antigens, even if relative positions/orientations of individual epitopes of antigens are irregular, facilitating formation of aggregates for phagocytic uptake and elimination. In immunoFETs using intact IgGs as receptors, hinge flexibility should allow positioning of bound analytes in a distribution of orientations/proximities relative to the rest of the antibody and to the immunoFET sensing channel. This should occur whether antibodies are consistently oriented on sensing channel surfaces or not.

Individual antibodies bind specific single epitopes of protein antigens, typically 10-12 amino acids long, often contiguous in antigen sequence. Through the use of antibody fragments, to remove flexible hinge regions and reduce overall size, it may be possible to preferentially position specific charged regions of analytes proximal to sensing surfaces. This may allow for the detection of specific charged regions of analytes as opposed to detection of analyte net charge. Use of epitopespecific orientation could lead to the detection of net neutral proteins via exploitation of more highly charged regions.

Also, in the absence of specific affinity elements or chemoselective conjugation, surface adsorption of antibodies is not consistently oriented. No biochemical process forces antibodies to adsorb exclusively via the C3 (or any other) antibody domain:consistent alignment on surfaces requires modification of antibodies or surfaces. As for most immunoFETs, alignment of antibodies relative to sensing channels was not attempted here, but may have potentially interesting consequences.

Since adsorption does not occur exclusively at any specific antibody domain, the calculated distance between the sensing surface and bound charges, determined assuming uniform antibody adsorption to the surface by antibody C3 domains, and comparison of that distance with the predicted Debye length (the distance over which counter-ion shielding should occur) in physiological buffer cannot be relevant to immunoFET feasibility. However, the comparison (bound analyte charges to sensing surface distance to Debye length) is the crux of the classical infeasibility argument. Hence, the infeasibility argument as originally formulated is not germane to behaviour of immunoHFETs made in this fashion. That said, interfacial film structure is a determinant of sensitivity, though not in the manner classical immunoFET assessment suggests.

Film morphology determines analyte charge to sensing channel distance, and, thus, immunoFET sensitivity. Consistent with theory, immuno- and bioFET signal magnitude is highly dependent on analyte charge to sensing channel proximity. Isrealachvili (Intermolecular and surface forces, 1992, 2nd edn. London, UK: Academic Press) has predicted that FET signal magnitude varies with the sixth power of charge-to-surface distance. The mean distance of analyte charge to HFET surface cannot be determined with sufficient accuracy to empirically validate Isrealachvili's prediction with these immunoFETs, though it is clear that nanometer-scale changes in film thickness, and in position of bound analytes in interfaces, profoundly influence signal magnitude.

Figure 7A:
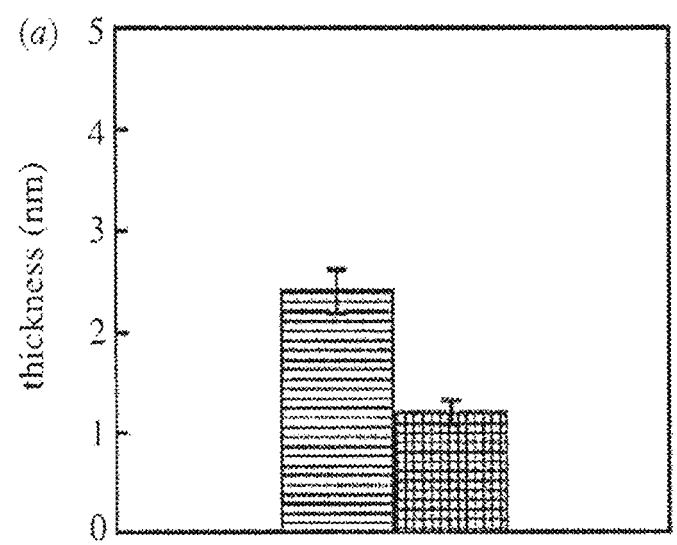
FIG. 7A-7B illustrate that interfacial silane films exhibit differential thickness and roughness as a function of their siloxane valency. Silane deposition protocols for APTES and APDMES were the same as those described for TEA in Example 1.
Figure 7B:
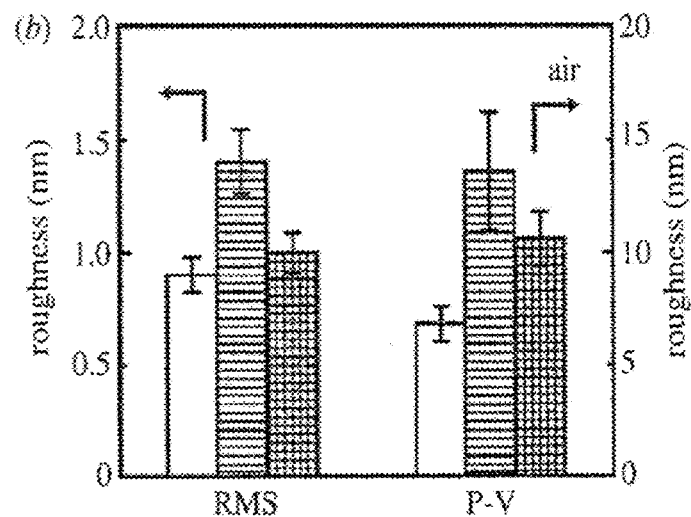

The sensors here were not engineered to minimize analyte-to-channel distance and maximize sensitivity, but this critical parameter can be addressed by multiple means. First, the sensor interfaces presented in this work use a trivalent silane (TEA) that is similar to APTES. Therefore, the interfacial height of the TEA layer should be higher than the minimal height achieved using a monovalent silane derivative (e.g., as with aminopropyl dimethylethoxy silane (APDMES). In comparison with films made with trivalent silanes, monovalent silanes form thinner polymer films with more regular (smoother) surfaces, shown in FIGS. 7A-7B. Based on differential sensitivity observed using APTES (trivalent) and APDMES (monovalent) interfacial polymers, the sensitivity of the presented devices can be enhanced by depositing more ideal (i.e., thinner, more regular) interface built using monovalent silanes. That said, the sensitivity of the unoptimized immunoHFETs demonstrated here was sufficient to allow us to demonstrate immunoHFET feasibility in a physiological environment.

Shielding of charges of bound analytes by buffer ions indeed occurs in immunoFETs, but the key issue for immunoHFET feasibility is whether charges of any given analyte bound to antibody receptors of an immunoHFET are shielded by ions in physiological buffers beyond detection by the underlying FET. This is a complex consideration (encompassing analyte charge density, charge distribution, specific receptor and analyte three-dimensional structures, specific receptor epitope recognition properties, receptor bioconjugation conditions, interfacial film morphology, sensor dielectric thickness, specifics of sensor operation, etc.), dependent on particulars of the immuno- or bioFET at hand.

Orientation of affinity elements might drive differences in HFET performance should differential orientation influence positions of analyte charges relative to the sensing channel. Interfaces with regular affinity element orientation can be constructed. Assuming the validity of theoretical exponential charge-to-surface distance relationships, it may be possible to use oriented, rigid affinity elements to build immunoFETs that detect specific analyte charges or regions of charge in preference to or exclusion of others. ImmunoHFETs using intact antibodies, and perhaps even some antibody fragments, as receptor may not allow for detection of specific charged regions of analytes owing to antibody (IgG) conformational freedom. Intact IgGs should hold analytes in a distribution of orientations and distances relative to the surface, even if antibody binding to the FET surface was exclusively via the IgG antibody C3 domain, as was originally, but inaccurately, assumed in classical immunoFET analysis.

AlGaN/GaN HFETs may be particularly suited to use in high osmolarity environments (as in vivo) because of limited AlGaN permeability to buffer ions and high-electron current drive properties. Other FETs with, or engineered to have, similar properties may be as efficacious and more economical. ImmunoFET economy and ease of fabrication may be important, as potential for immunoFET sensors in clinical applications is large. Given economical FET platforms, immunoFET assay could potentially supplant more laborious, time-consuming and expensive immunoassays in clinical and laboratory settings.

Example 2

Detection of IP-10, CXCL9, RANTES, and Streptavidin in Physiological Conditions Using FET-based Sensors AlGaN/GaN HFETs were prepared as described in Example 1, and surface functionalized with triethoxysilane aldehyde (TEA) to create a thin silane layer bearing a terminal aldehyde. The functionalized devices were then incubated with 1 µg/ml of an IgG antibody directed towards a target protein (CXCL10, CCL5, or streptavidin). Free amines on the IgG bind to the terminal aldehydes to decorate the sensor surface with IgG receptors, creating an immunoHFET device.

The immunoHFET was first exposed to PBS and the device characteristics (drain current vs. drain voltage) was measured to establish a baseline. The solution of protein in PBS was then applied to the device and incubated for 5 minutes. The device characteristics was then measured for comparison to the baseline measurement. The change between these two measurements was due to modulation of the source/drain current by the presence of the charges on the target protein been bound to the sensor surface receptors. Control experiments were also performed using the device without IgG receptors bound to the surface. In the absence of an IgG recognition element, no change in signal was observed (consistant with analyte not binding to the sensor)

Figure 8:
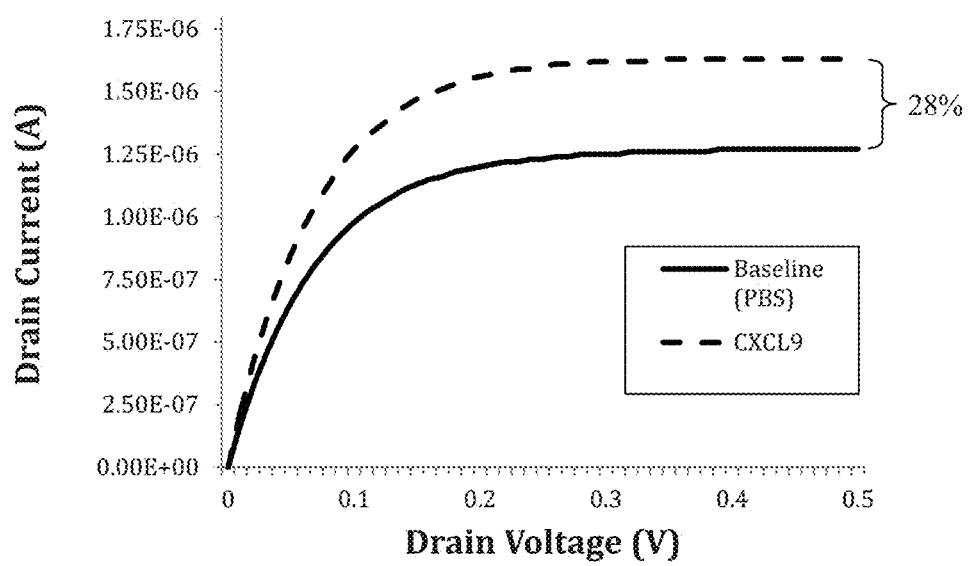
FIG. 8 is a plot of the device characteristics (drain current (A) as a function of drain voltage (V)) for an immunoHFET functionalized with Anti-CXCL9 (anti-MIG) IgG antibodies upon immersion in PBS (solid trace) and immersion in a solution of CXCL9 (MIG) (10 ng/ml, dashed trace) in PBS. The percent change in signal (current) is indicated on the graph (~28%).

As described in Example 1, chemokine CXCL9 (also known as MIG) could be detected using sensors containing anti-CXCL9 IgG antibodies bound to the surface of the immunoFET. This was further demonstrated first exposing the containing anti-CXCL9 IgG antibodies to PBS for the baseline measurement, and then exposing the sensors to CXCL9 at 10 ng/ml in PBS. The device characteristics (drain current (A) as a function of drain voltage (V)) for an immunoHFET were measured upon immersion in PBS (FIG. 8, solid trace) and immersion in a solution of CXCL9 (MIG) (10 ng/ml, FIG. 8, dashed trace) in PBS. The percent change in signal (current) was approximately 28%.

CXCL9 (IP-10)

Figure 9:
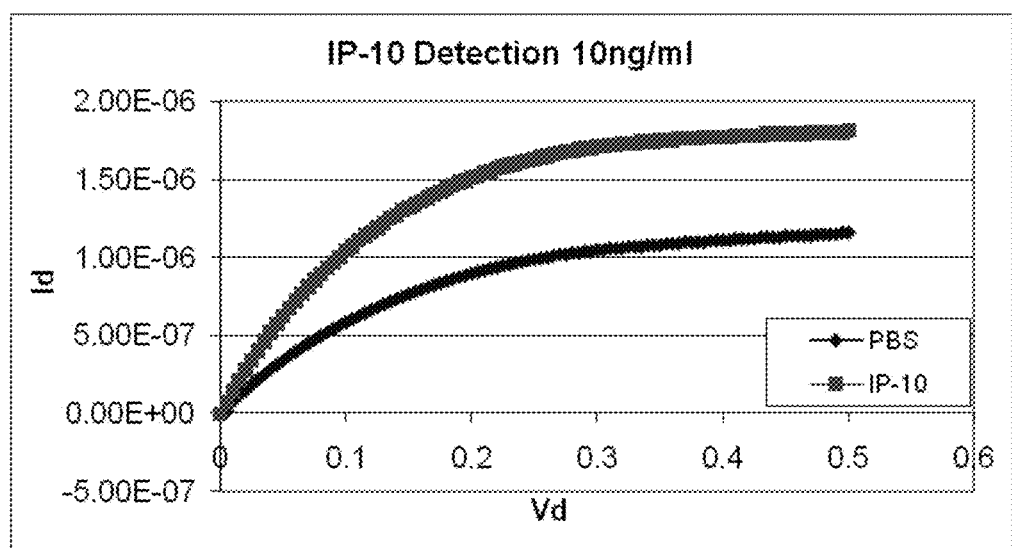
FIG. 9 is a plot of the device characteristics (drain current (A) as a function of drain voltage (V)) for an immunoHFET functionalized with Anti-CXCL10 IgG antibodies upon immersion in PBS (diamond trace) and immersion in a solution of CKCL10 (IP-10) (10 ng/ml, square trace) in PBS. The percent change in signal (current) was approximately 41%.

Anti-CXCL10 IgG antibodies were bound to the surface of the immunoFET sensors as a receptor for the chemokine CXCL10 (also known as IP-10). CXCL10 has a net charge of +1 at pH 7.4 (17 positive charges/molecule) and a molecular weight of 8.6 kDa. These functionalized sensors were first exposed to PBS for the baseline measurement, and were then exposed to CXCL10 at 10 ng/ml in PBS for the experimental measurement. At this concentration level and for this analyte, the average percent change in signal from the baseline was ~+41% (n=4). Control experiments performed using the device without IgG receptors showing an average change in signal from the baseline of ~+4%. The results are shown in FIG. 9.

CCL5 (RANTES)

Anti-CCL5 IgG antibodies were bound to the surface of the immunoFET sensors as a receptor for the chemokine CCL5 (also known as RANTES). CCL5 has a net charge of +6 at pH 7.4 (11 positive charges/molecule) and a molecular weight of 7.8 kDa. These functionalized sensors were first exposed to PBS for the baseline measurement, and were then exposed to CCL5 at 10 ng/ml in PBS for the experimental measurement. At this concentration level and for this analyte, the average percent change in signal from the baseline was ~+16% (n=3). Control experiments performed using the device without IgG receptors showing an average change in signal from the baseline of ~+2%.

Streptavidin

Anti-streptavidin IgG antibodies were bound the surface of immunoFET sensors as a receptor for the protein streptavidin. Streptavidin has a net charge of approximately −6 at pH 7.4 and a molecular weight of approximately 60 kDa (tetrameric protein composed of four identical subunits of ~15 kDa). These functionalized sensors were first exposed to PBS for the baseline measurement, and were then exposed to streptavidin at 10 ng/ml in PBS for the experimental measurement. At this concentration level and for this analyte, the average percent change in signal from the baseline ranged was ~−24% (n=3). Control experiments performed using the device without IgG receptors showing an average change in signal from the baseline of ~+20/%.

Streptavidin detection was performed to demonstrate detection of a protein of a negative charge. The previous analytes (CXCL9, CXCL10, CCL5) all exhibit a net positive charge at pH 7.4, so streptavidin was used to show that the immunoHFET is capable of detecting proteins of both positive and negative net charges. Where we measured an increase in current from baseline for the positively charged analytes, a decrease in current is as expected for our n-type AlGaN/GaN HFET device and a negatively charged analyte. The binding of negatively charged analyte proximal to the sensor surface decreases the conduction of the negatively charged electrons in the device, resulting in a decrease in drain current.

Example 3

Detection of CXCL9 in the Urine of Patients Following Kidney Transplantation

As discussed above, chemokine CXCL9 is associated with transplant rejection. Normal CXCL9 levels in urine should be low (zero to de minimus in the case of healthy persons and non-rejecting patients). However, in the case of patients rejecting kidney transplants, CXCL9 levels in urine can range from about 100-1000 pg/mL.

The ability of sensors containing anti-CXCL9 IgG antibodies bound to the immunoFET surface to detect clinically relevant levels of CKCL9 in the urine of transplant patients was evaluated. Urine samples were collected from two consenting patients (patient 004 and patient 005) who had recently received kidney transplants. Urine samples were collected when patients 004 and 005 returned following surgery for biopsies to assess transplant rejection. Following collection, the urine samples were stored at −80° C. until analysis.

Chemokine CXCL9 in the urine samples was detected using sensors containing anti-CXCL9 IgG antibodies bound to the surface of the immunoFET. Briefly, the immunoFET sensor was first exposed to PBS, and the device characteristics (drain current vs. drain voltage) was measured to establish a baseline in PBS. The sensor was then placed in the urine sample to allow for binding between the recognition element (anti-CXCL9 IgG antibody) and the analyte of interest (CXCL9). The device was then returned to a PBS environment, and the device characteristics were measured for comparison to the baseline measurement. The device was returned to a PBS environment for measurement to ensure that the testing buffer is the same as the baseline to allow for the most accurate comparison. The percent change between these two measurements (% Change in Signal from Baseline) was due to modulation of the source/drain current by charges on the target protein bound to the sensor surface. The results are shown in Table 1.

In parallel, an ELISA assay was performed on all urine samples to detect CXCL9 levels. As seen in Table 2, the ELISA results were consistent with the measurements observed by immunoFET.

TABLE 1

Results of immunoFET analysis of urine samples

| Patient | Sample No. | % Change in Signal from Baseline | |
|---|---|---|---|
| 004 | 1 | 49.59† | |
| 004 | 2 | 8.37 | |
| 004 | 3 | 7.89 | |
| | | 004 Avg = | 21.95 |
| | | 004 Avg (minus first test) = | 8.13 |
| 005 | 1 | 8.85 | |
| 005 | 2 | −2.73 | |
| 005 | 3 | 0.74 | |
| 005 | 4 | −7.69 | |
| | | 005 Avg = | −0.2075 |

†Appears to be an anomalous reading. 004 Average value was computed without this value.

TABLE 2

Results of ELISA for CXCL9 in urine samples

| Sample | Absorbance |
|---|---|
| 004 Avg | 0.16 |
| 005 Avg | 0.06 |
| Background (no pAb) | 0.05 |
| Control (no sample) | 0.04 |
| Standard - 2000 pg/ml CXCL9 | 0.20 |
| Standard - 500 pg/ml CXCL9 | 0.08 |
| Standard - 125 pg/ml CXCL9 | 0.06 |

Patient 004 exhibited a change in signal from the baseline (004 Avg=8.13%), suggesting the presence of CXCL9 in the urine. Little to no response was observed in the case of patient 005, suggesting de minimus levels of CXCL9 in the urine. Importantly, patient 004 went on to clinical rejection, whereas patient 005 did not. This suggests that anti-CXCL9 immunoHFET analysis of urine can detect rejection of transplanted kidneys, and can differentiate rejection from other causes of kidney dysfunction.

The sensors, devices, and methods of the appended claims are not limited in scope by the specific sensors, devices, and methods described herein, which are intended as illustrations of a few aspects of the claims. Any sensors, devices, and methods that are functionally equivalent are intended to fall within the scope of the claims. Various modifications of the sensors, devices, and methods in addition to those shown and described herein are intended to fall within the scope of the appended claims. Further, while only certain representative sensors, devices, and methods steps disclosed herein are specifically described, other combinations of the sensors, devices, and methods also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A sensor comprising:
   a) a substrate;
   b) a channel disposed on the substrate, wherein the channel is substantially impermeable to ions under physiological conditions;
   c) a source electrode and a drain electrode electrically connected to the channel, wherein the source electrode and the drain electrode are formed to be separate such that the channel forms a path for current flow between the source electrode and the drain electrode; and
   d) a recognition element for an analyte of interest covalently immobilized on the surface of the channel via a linking group;
   wherein the recognition element comprises an antibody or an antibody fragment; and
   wherein the distance between the recognition element and the channel is configured such that association of the analyte of interest with the recognition element induces a change in the electrical properties of the channel.

2. The sensor of claim 1, wherein the substrate is selected from the group consisting of Si, SiC, Al2O3, Group III-nitrides, ZnO, MgZnO, glass, diamond, and combinations thereof.

3. The sensor of claim 2, wherein the channel comprises a Group III-nitride heterojunction,
   wherein the Group III-nitride heterojunction comprises a first Group III-nitride layer and a second Group III-nitride layer, and
   wherein the first Group III-nitride layer and the second Group III-nitride layer have different bandgaps, such that a two-dimensional electron gas is generated inside the Group III-nitride heterojunction.

4. The sensor of claim 3, wherein the first Group III-nitride layer comprises a material selected from the group consisting of GaN, InN, InGaN, AlGaN, and combinations thereof, and the second Group III-nitride layer comprises a material selected from the group consisting of AlGaN, AlN, InAlN, GaN, and combinations thereof.

5. The sensor of claim 4, wherein the first Group III-nitride layer comprises GaN and the second Group III-nitride body comprises AlGaN.

6. The sensor of claim 1, wherein the linking group is selected such that the distance between the recognition element and the surface of the channel is less than about 10 nm.

7. The sensor of claim 1, wherein the linking group comprises a polyvalent linking group.

8. The sensor of claim 1, wherein the linking group comprises a monovalent linking group.

9. A method for detecting an analyte of interest comprising:

a) contacting the analyte of interest with a sensor defined by claim 1.

10. The method of claim 9, further comprising measuring a change in an electrical property of the channel to determine a presence of the analyte of interest, to determine the concentration of the analyte of interest, or a combination thereof,
 wherein the change in electrical property comprises a change in current flow, a change in voltage, a change in impedance, or combinations thereof.

11. The method of claim 10, wherein the analyte of interest comprises a biomarker for a disease process in a patient.

12. The method of claim 11, wherein the analyte of interest is a protein.

13. The method of claim 10, wherein the analyte of interest comprises a macromolecule.

14. The method of claim 9, wherein the analyte of interest comprises a bacteria.

15. A probe for detecting an analyte of interest, the probe comprising:
 a) an elongate member having a proximal end and a distal end; and
 b) one or more sensors defined by claim 1 positioned at the distal end of the elongate member,
 wherein the one or more sensors comprise recognition elements that selectively associate with the analyte of interest.

16. A multi-well plate comprising:
 a) a base comprising a first material having a substantially co-planar top and bottom surface;
 b) a plurality of microwells disposed in the base, wherein each microwell comprises a solid bottom proximal to the bottom surface of the base, one or more solid side walls, and an opening located on the top surface of the base; and
 c) a sensor defined by claim 1 positioned within one or more of the plurality of microwells, and configured such that the recognition element of the sensor is in contact with the contents of the microwell in which it is positioned.

17. The sensor of claim 1, wherein the distance between the recognition element and the channel is configured such that association of the analyte of interest with the recognition element in a physiological buffer solution induces a change in the electrical properties of the channel.

18. The sensor of claim 1, wherein the channel is fabricated from a material that is substantially impermeable to ions, such that the sensor exhibits a drift in current flow of less than about 20% over a period of 10 hours when immersed in a physiological buffer solution.

19. The sensor of claim 1, wherein the sensor further comprises a gate electrode configured to apply a gate bias to the channel.

20. A method for monitoring a graft recipient for a rejection response, the method comprising
 contacting the graft or fluid adjacent to the graft in situ with a probe comprising an elongate member having a proximal end and a distal end; and one or more sensors positioned at the distal end of the elongate member,
 wherein each of the one or more sensors comprise:
 a) a substrate;
 b) a channel disposed on the substrate, wherein the channel is substantially impermeable to ions under physiological conditions;
 c) a source electrode and a drain electrode electrically connected to the channel, wherein the source electrode and the drain electrode are formed to be separate such that the channel forms a path for current flow between the source electrode and the drain electrode; and
 d) a recognition element that selectively associates with a biomarker for graft rejection immobilized on the surface of the channel;
 wherein the distance between the recognition element and the channel is configured such that association of the analyte of interest with the recognition element induces a change in the electrical properties of the channel.

\* \* \* \* \*